(12) United States Patent
Cunningham et al.

(10) Patent No.: US 11,992,517 B2
(45) Date of Patent: *May 28, 2024

(54) COMPOSITIONS AND METHODS FOR PROMOTING THE MINERALIZATION OF BIOLOGICAL TISSUE

(71) Applicant: NEW YORK SOCIETY FOR THE RUPTURED AND CRIPPLED MAINTAINING THE HOSPITAL FOR SPECIAL SURGERY, New York, NY (US)

(72) Inventors: Matthew E. Cunningham, Manhasset, NY (US); Agata Krzyzanowska, Brooklyn, NY (US)

(73) Assignee: NEW YORK SOCIETY FOR THE RELIEF OF THE RUPTURED AND CRIPPLED, MAINTAINING THE HOSPITAL FOR SPECIAL SURGERY, New York, NY (US)

( * ) Notice: Subject to any disclaimer, the term of this patent is extended or adjusted under 35 U.S.C. 154(b) by 558 days.

This patent is subject to a terminal disclaimer.

(21) Appl. No.: 16/368,042

(22) Filed: Mar. 28, 2019

(65) Prior Publication Data

US 2019/0282672 A1 Sep. 19, 2019

Related U.S. Application Data

(63) Continuation of application No. 15/028,997, filed as application No. PCT/US2014/060654 on Oct. 15, 2014, now Pat. No. 10,293,031.

(Continued)

(51) Int. Cl.
| | | |
|---|---|---|
| C12N 5/077 | (2010.01) |
| A61K 9/00 | (2006.01) |
| A61K 31/195 | (2006.01) |
| A61K 31/675 | (2006.01) |
| A61K 31/7076 | (2006.01) |
| A61K 31/7088 | (2006.01) |
| A61K 31/713 | (2006.01) |
| A61K 35/32 | (2015.01) |
| A61K 38/19 | (2006.01) |
| A61K 38/20 | (2006.01) |
| A61K 38/46 | (2006.01) |
| A61K 39/00 | (2006.01) |
| A61K 45/06 | (2006.01) |
| A61K 48/00 | (2006.01) |
| A61L 27/36 | (2006.01) |
| A61L 27/38 | (2006.01) |

(Continued)

(52) U.S. Cl.
CPC .......... *A61K 38/465* (2013.01); *A61K 9/0019* (2013.01); *A61K 9/0085* (2013.01); *A61K 31/195* (2013.01); *A61K 31/675* (2013.01); *A61K 31/7076* (2013.01); *A61K 31/7088* (2013.01); *A61K 31/713* (2013.01); *A61K 35/32* (2013.01); *A61K 38/191* (2013.01); *A61K 38/2006* (2013.01); *A61K 39/00* (2013.01); *A61K 45/06* (2013.01); *A61K 48/00* (2013.01); *A61L 27/3658* (2013.01); *A61L 27/3687* (2013.01); *A61L 27/3821* (2013.01); *A61L 27/3856* (2013.01); *A61L 27/3895* (2013.01); *A61L 27/54* (2013.01); *A61L 27/58* (2013.01); *C07K 14/4702* (2013.01); *C12N 5/0655* (2013.01); *C12N 15/1138* (2013.01); *C12N 15/86* (2013.01); *A61L 2300/412* (2013.01); *A61L 2300/45* (2013.01); *A61L 2300/604* (2013.01); *A61L 2300/64* (2013.01); *A61L 2400/06* (2013.01); *A61L 2430/38* (2013.01); *C12N 2310/122* (2013.01); *C12N 2310/14* (2013.01); *C12N 2310/531* (2013.01); *C12N 2320/31* (2013.01); *C12N 2320/32* (2013.01); *C12N 2501/2301* (2013.01); *C12N 2501/73* (2013.01); *C12N 2740/16043* (2013.01); *C12Y 301/03001* (2013.01)

(58) Field of Classification Search
None
See application file for complete search history.

(56) References Cited

U.S. PATENT DOCUMENTS

| | | | | |
|---|---|---|---|---|
| 2002/0183276 A1* | 12/2002 | Millan | ............... | C07K 14/705 514/44 A |
| 2004/0023916 A1* | 2/2004 | Millan | ............... | C07K 16/40 514/565 |

(Continued)

FOREIGN PATENT DOCUMENTS

| | | |
|---|---|---|
| EP | 1303588 | 10/2012 |
| WO | WO 2012/123028 | 9/2012 |

OTHER PUBLICATIONS

Chung et al, Mechanism of Action of I-Glycerophosphate on Bone Cell Mineralization, Calcif Tissue Int (1992) 51:305-311.*

(Continued)

*Primary Examiner* — Maria Marvich
(74) *Attorney, Agent, or Firm* — Leason Ellis LLP

(57) ABSTRACT

This invention relates to compositions and methods for activating and promoting mineralization in tissue that does not normally mineralize, specifically intervertebral discs. The composition comprises agents that increase the expression of the gene that encodes TNAP and/or the activation, amount or activity of TNAP protein, and agents that decrease the expression of ANK and/or ENPP and/or the activation, amount or activity of these proteins. The composition can be in the form of a cell or cells. The invention also relates to methods of using the composition.

4 Claims, 24 Drawing Sheets

Specification includes a Sequence Listing.

Related U.S. Application Data

(60) Provisional application No. 61/891,632, filed on Oct. 16, 2013.

(51) Int. Cl.

| | |
|---|---|
| *A61L 27/54* | (2006.01) |
| *A61L 27/58* | (2006.01) |
| *A61P 19/02* | (2006.01) |
| *C07K 14/47* | (2006.01) |
| *C12N 5/10* | (2006.01) |
| *C12N 15/11* | (2006.01) |
| *C12N 15/113* | (2010.01) |
| *C12N 15/55* | (2006.01) |
| *C12N 15/86* | (2006.01) |

(56) References Cited

U.S. PATENT DOCUMENTS

| | | |
|---|---|---|
| 2004/0228900 A1 | 11/2004 | Murphy et al. |
| 2009/0053192 A1 | 2/2009 | Millan et al. |
| 2010/0239634 A1 | 9/2010 | Shimp et al. |
| 2013/0079881 A1 | 3/2013 | Bonassar et al. |

OTHER PUBLICATIONS

Liedtke et al, Tissue-Nonspecific Alkaline Phosphatase—A Gatekeeper of Physiological Conditions in Health and a Modulator of Biological Environments in Disease, Biomolecules 2020, pp. 1-20.*
He et al, Gene Expression Profile of Hypertrophic Chondrocytes Treated with H2O2: A preliminary Investigation, Chinese Medical Sciences Journal, 2018, pp. 45-52.*
Van der Kraan and van den Berg, Chondrocyte hypertrophy and osteoarthritis: role in initiation and progression of cartilage degeneration?, Osteoarthritis and Cartilage, 2012, pp. 223-232.*
Yi et al, Gene expression profiling of chondrogenic differentiation by dexamethasone-conjugated polyethyleneimine with SOX trio genes in stem cells, Stem Cell Research & Therapy (2018), pp. 1-13.*
Wu et al, Proteolysis Involving Matrix Metalloproteinase 13 (Collagenase-3) Is Required for Chondrocyte Differentiation That Is Associated with Matrix Mineralization, Journal of Bone and Mineral Research, 2002, pp. 639-651.*
Gerstenfeld and Landis, Gene Expression and Extracellular Matrix Ultrastructure of a Mineralizing Chondrocyte Cell Culture System, The Journal of Cell Biology, vol. 112, No. 3, Feb. 1991 501-513.*
Ambros, "The functions of animal microRNAs", (Sep. 2004) Nature 431 :350.
Anderson, "Matrix Vesicles and Calcification", (Jun. 2003) Current Rheumatol. Reports 5:222.
Baroy el al., "shRNA Expression Constructs Designed Directly from siRNA Oligonucleotide Sequences", (Jan. 30, 2010) Mol. Biotechnol. 45: 1 16.
Bartel, "MicroRNA Target Recognition and Regulatory Functions", (Jan. 23, 2009) Cell 136:215-233.
Buchet et al., "Isolation and Characteristics of Matrix Vesicles", (Jun. 27, 2013) Methods in Molecular Biology 1053 : 115.
Cheng and Pritzker, "Pyrophosphate, Phosphate Ion Interaction: Effects on Calcium Pyrophosphate and Calcium Hydroxyapatite Crystal Formation in Aqueous Solutions", (May 26, 1983) J. Rheum. pp. 769-777.
DiMauro et al., "Kinetic Characterization of Hypophosphatasia Mutations With Physiological Substrates", (Feb. 6, 2002) J. Bone Miner. Res. 17: 1383.
Gurley et al., "Mineral Formation in Joints Caused by Complete or Joint-Specific Loss of ANK Function", (May 30, 2006) J. Bone. Miner. Res. 21: 1238.
Gregory et al., "An Alizarin red-based assay of mineralization by adherent cells in culture: comparison with cetylpyridinium chloride extraction", (Apr. 20, 2004) Analytical Biochemistry 329:77.
Krebs et al., "Calcium phosphate-DNA nanoparticle gene delivery from Alginate hydrogels induces in vivo osteogenesis", (Mar. 25, 2009) J. Biomed. Material Res. 92: 1 131.
Koshizuka et al., "Isolation of novel mouse genes associated with ectopic ossification by differential display method using ttw, a mouse model for ectopic ossification", (2001) Cytogenet. Cell Genet. 94: 163.
Minogue et al., "Characterization of the Human Nucleus Pulposus Cell Phenotype and Evaluation of Novel Marker Gene Expression to Define Adult Stem Cell Differentiation", (Dec. 2010) Arthritis and Rheumatism 62:3695.
Murshed et al., "Unique coexpression in osteoblasts of broadly expressed genes accounts for the spatial restriction of ECM mineralization to bone", (Mar. 14, 2005) Genes and Development 19: 1093.
Ong et al., "Projections to 2030 of the Prevalence of Primary and Revision Spine Fusions in the U.S.", (Feb. 2007) Orthopedic Research Society, 53rd Annual Meeting.
Rajaee et al., "Spinal Fusion in the United States", (Jan. 2012) Spine 37:67.
Rutsch et al., "Mutations in ENPP1 are associated with 'idiopathic' infantile arterial calcification", (Aug. 2003) Nature Genetics 34:379.
Skubutyte et al., "Hypoxia-Inducible Factor Regulation of ANK Expression in Nucleus Pulposus Cells", (Sep. 2010) Arthritis and Rheumatism 62:2707.
Zhao et al., "Activation of nuclear factor-kappa B accelerates vascular calcification by inhibiting ankyloses protein homolog expression", (Mar. 21, 2012) Kidney International 82:34.
Shioi et al., Induction of Bone-Type Alkaline Phosphatase in Human Vascular Smooth Muscle Cells, Circulation Research, Jun. 5, 2002, pp. 9-16 plus supplementary pp. 1-9.

* cited by examiner

COMPOSITIONS AND METHODS FOR PROMOTING THE MINERALIZATION OF BIOLOGICAL TISSUE

CROSS-REFERENCE TO OTHER APPLICATIONS

This application is a continuation of U.S. Non-Provisional patent application Ser. No. 15/028,997, filed Apr. 13, 2016, now U.S. Pat. No. 10,293,031, issued May 21, 2019, which is a U.S. National Phase Application under 35 U.S.C. § 371 of International Patent Application No. PCT/US14/60654, filed Oct. 15, 2014, which claims priority to U.S. Provisional Patent Application No. 61/891,632, filed Oct. 16, 2013, each of which is hereby incorporated by reference as if expressly set forth in their respective entirety herein.

FIELD OF THE INVENTION

The present invention relates to compositions and methods for promoting mineralization in biological tissue, in particular intervertebral disc. In particular, the compositions and methods of the present invention promote the intervertebral discs to mineralize into bone, which allows the fusing the two adjoining spinal discs, i.e., spinal fusion, without surgical intervention.

BACKGROUND OF THE INVENTION

The intervertebral discs act as cushions between vertebral bodies. Intervertebral discs comprise cartilaginous endplates, made up of 55% water, 8% proteoglycan, and 25% collagen, nucleus pulposus, made up of 77% water, 14% proteoglycan, and 4% collagen, and annulus fibrosus, made up of 70% water, 5% proteoglycan, and 15% collagen.

As discs age, degeneration occurs. The disc loses height causing pressure on the spinal cord and/or nerves which leads to pain, loss of osmotic pressure in the nucleus, tearing in the annulus, and nuclear material to leak out of the outer rim of the annulus.

Patients whose symptoms do not improve with medications and non-operative treatments such as physical therapy, and patients with severe spinal deformity, instability, or end-stage arthritis are definitively managed with surgery to cause the vertebrae of the spine to weld together, in a procedure called fusion. Spine fusion eliminates motion between the vertebrae, by allowing bone bridges to form between them. Over 400,000 patients undergo spinal fusion each year (Coe et al. (2006); Ong et al. (2007); Rajace et al. (2012)).

This bony-bridging and fusion is accomplished using surgeries that can last several hours, and have high rates of associated complications, pain and suffering, and high costs (both from care delivered and lost days at work). Additionally, in greater of 20% of the surgeries, there is a failure to relieve lower back pain symptoms. In approximately 5 to 10% of surgeries, there is a failure of fusion known as pseudarthrosis. There is also a risk of excessive blood loss, infection, pain at the graft site, graft rejection, blood clots, and nerve injury.

A better method to produce spine fusions is needed, which would allow spine fusions to be created more economically, with less risk to the patient, and less cost to society.

SUMMARY OF THE INVENTION

The present invention overcomes the problems in the art by providing novel compositions and methods for spine fusion. The compositions and methods of the present invention are based upon the surprising discovery that the cells in the intervertebral disc can be induced to mineralize.

One embodiment of the present invention is a composition comprising an agent or agents that increase or up-regulate the expression of the gene encoding TNAP, and/or increase or promote the activation, amount and/or activity of the TNAP protein, and further comprising an agent or agents that decrease or down-regulate the expression of the gene encoding ANK, and/or decrease, prevent or block the activation, amount and/or activity of the ANK protein. The preferred agent for increasing the expression of the gene encoding TNAP is a nucleic acid which encodes the TNAP protein, or the entire TNAP gene, or a nucleic acid that is substantially homologous to the TNAP gene, or a variant, mutant, fragment, homologue or derivative of the TNAP gene that produces a protein that maintains or increases the function of changing the ratio of ePPi to ePi. The preferred agents for decreasing or down-regulating the expression of the gene encoding ANK is TNF-α or IL-1β. The TNF-α or IL-1β protein itself can be added to the composition or a nucleic acid encoding the protein can be used. Another preferred agent for decreasing or down-regulating the expression of ANK is an interfering RNA of ANK.

A further embodiment of the present invention is a composition comprising an agent or agents that increase or up-regulate the expression of the gene encoding TNAP, and/or increase or promote the activation, amount and/or activity of the TNAP protein and further comprising an agent or agents that decrease or down-regulate the expression of the gene encoding ENPP, and/or decrease, prevent or block the activation, amount and/or activity of the ENPP protein. The preferred agent for increasing the expression of the gene encoding TNAP is a nucleic acid which encodes the TNAP protein, or the entire TNAP gene, or a nucleic acid that is substantially homologous to the TNAP gene, or a variant, mutant, fragment, homologue or derivative of the TNAP gene that produces a protein that maintains or increases the function of changing the ratio of ePPi to ePi. The preferred agents for decreasing or down-regulating the expression of the gene encoding ENPP is TNT-α or IL-1β. The protein TNF-α or IL-1β itself can be added to the composition or a nucleic acid encoding the protein can be used. Another preferred agent for decreasing or down-regulating the expression of ENPP is an interfering RNA of ENPP.

The composition of the present invention can take many forms. One form is a cell or cells comprising the agent or agents that increase or up-regulate the expression of the gene encoding TNAP, and/or increase or promote the activation, amount and/or activity of the TNAP protein, and further comprising an agent or agents that decrease or down-regulate the expression of the genes encoding ANK and/or ENPP, and/or decrease, prevent or block the activation, amount and/or activity of the ANK and/or ENPP protein. These cell or cells can be prokaryotic or eukaryotic. In one embodiment, the cell or cells are bovine nucleus pulposus cells.

One embodiment of the present invention, the composition is a cell or cells comprising a nucleic acid which encodes the TNAP protein, or the entire TNAP gene, or a nucleic acid that is substantially homologous to the TNAP gene, or a variant, mutant, fragment, homologue or derivative of the TNAP gene that produces a protein that maintains or increases the function of changing the ratio of ePPi to ePi, and TNF-α, either in the form of a protein or as a nucleic acid encoding the protein.

A further embodiment of the composition is a cell or cells comprising a nucleic acid which encodes the TNAP protein, or the entire TNAP gene, or a nucleic acid that is substantially homologous to the TNAP gene, or a variant, mutant, fragment, homologue or derivative of the TNAP gene that produces a protein that maintains or increases the function of changing the ratio of ePPi to ePi, and IL-1β, either in the form of a protein or as a nucleic acid encoding the protein.

A further embodiment of the composition is a cell or cells comprising a nucleic acid which encodes the TNAP protein, or the entire TNAP gene, or a nucleic acid that is substantially homologous to the TNAP gene, or a variant, mutant, fragment, homologue or derivative of the TNAP gene that produces a protein that maintains or increases the function of changing the ratio of cPPi to ePi, and an interfering RNA to ANK.

Yet another embodiment of the composition is a cell or cells comprising a nucleic acid which encodes the TNAP protein, or the entire TNAP gene, or a nucleic acid that is substantially homologous to the TNAP gene, or a variant, fragment, homologue or derivative of the TNAP gene that produces a protein that maintains or increases the function of changing the ratio of ePPi to ePi, and an interfering RNA to ENPP.

The composition of the present invention can also comprise agent or agents that increase or up-regulate the expression of the gene encoding TNAP, and/or increase or promote the activation, amount and/or activity of the TNAP protein, and an agent or agents that decrease or down-regulate the expression of the genes encoding ANK and/or ENPP, and/or decrease, prevent or block the activation, amount and/or activity of the ANK and/or ENPP protein, in a pharmaceutical preparation.

The composition of the present invention can also comprise cells in a pharmaceutical composition.

The composition can also comprise other agents that facilitate migration, integration, regeneration, proliferation, and growth of cells into and around the injury or defect, and/or promote healing of the injury or defect, and/or are osteogenic, i.e., build, grow and produce bone.

These agents, include but are not limited to, cytokines, chemokines, chemoattractants, anti-microbials, anti-virals, anti-inflammatories, bone regenerator molecules, anti-immune agents, and combinations thereof.

Yet a further embodiment of the present invention is a method to treat, repair and/or replace defects and/or injuries to biological tissue, more specifically intervertebral discs, by administering the composition to a subject in need thereof.

A further embodiment is a method of activating and/or promoting mineralization of biological tissue, in particular, intervertebral discs by administering the composition to a subject in need thereof.

A further embodiment is a method of fusing two contiguous vertebrae by administering the composition of the present invention into the intervertebral disc between the two vertebrae in a subject in need thereof.

A further embodiment of the present invention is a kit comprising the composition, tools for administering the composition, and instructions.

Yet a further embodiment is the use of bovine NP cells, both native and those comprising an agent or agents that up-regulate the expression of TNAP or increase TNAP protein, and/or down-regulate the expression of ANK and/or ENPP or decrease ANK and/or ENPP protein, for drug screening for potential therapeutic agents and for basic research tools.

BRIEF DESCRIPTION OF THE FIGURES

For the purpose of illustrating the invention, there are depicted in drawings certain embodiments of the invention. However, the invention is not limited to the precise arrangements and instrumentalities of the embodiments depicted in the drawings.

DETAILED DESCRIPTION OF THE INVENTION

Figure 1B:
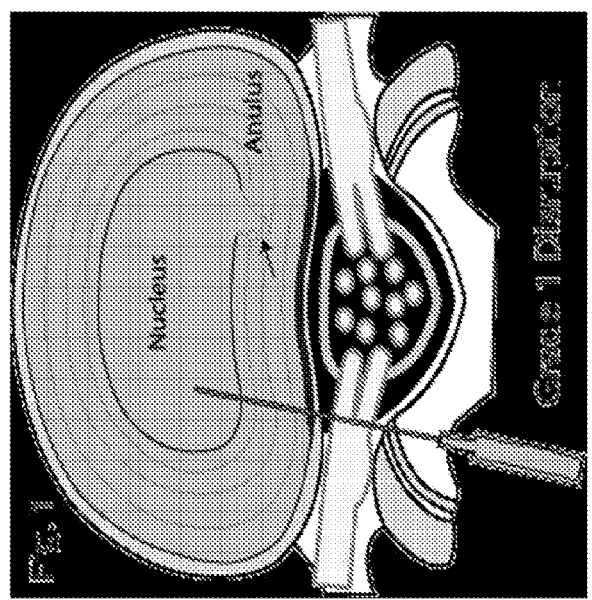
FIGS. 1A and 1B show two views of the intervertebral disc.

The present invention are compositions that when delivered into the disc space of the spine, are capable of converting the disc tissue into bone and thus inducing spine fusion. The compositions of the present invention can be delivered, placed or administered into the disc space of the spine by any method known in the art. The present invention also includes methods of using the compositions to induce mineralization in intervertebral discs, and fuse vertebrae without major surgical intervention. The compositions and methods are based on the novel finding that the up-regulation of TNAP and the down-regulation of ANK and/or ENPP leads to matrix mineralization in intervertebral discs.

Definitions

The terms used in this specification generally have their ordinary meanings in the art, within the context of this invention and the specific context where each term is used. Certain terms are discussed below, or elsewhere in the specification, to provide additional guidance to the practitioner in describing the methods of the invention and how to use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of the other synonyms. The use of examples anywhere in the specification, including examples of any terms discussed herein, is illustrative only, and in no way limits the scope and meaning of the invention or any exemplified term. Likewise, the invention is not limited to its preferred embodiments.

The term "agent" as used herein means a substance that produces or is capable of producing an effect and would include, but is not limited to, chemicals, pharmaceuticals, biologics, inorganic molecules, small organic molecules, antibodies, nucleic acids, peptides, and proteins.

The term "subject" as used in this application means an animal with an immune system such as avians and mammals. Mammals include canines, felines, rodents, bovine, equines, porcines, ovines, and primates. Avians include, but are not limited to, fowls, songbirds, and raptors. Thus, the invention can be used in veterinary medicine, e.g., to treat companion animals, farm animals, laboratory animals in zoological parks, and animals in the wild. The invention is particularly desirable for human medical applications The term "patient" as used herein means a human subject.

The term "in need thereof" would be a subject or patient known or suspected of having an injury to or defect in biological tissue, more specifically in the intervertebral disc, and more specifically a degeneration of the disc. Some conditions particularly suited for treatment would be end-stage disc degeneration, scoliosis, kyphosis, spondylolisthesis, and end-stage facet joint arthritis.

The terms "treat", "treatment", and the like refer to a means to slow down, relieve, ameliorate or alleviate at least one of the symptoms of the defect or injury or reverse the defect or injury after its onset.

The term "repair" and the like refer to any correction, reinforcement, reconditioning, remedy, making up for, making sound, renewal, mending, patching, or the like that restores function. Accordingly, the term "repair" can also mean to correct, to reinforce, to recondition, to remedy, to make up for, to make sound, to renew, to mend, to patch or to otherwise restore function.

The term "replace", "replacement", and the like refer to a means to substitute or take the place of defective or injured tissue.

The term "defect" and the like refer to a flaw or a physical problem in a structure, or system, especially one that prevents it from functioning correctly, or a medical abnormality. Defects can include, but are not limited to, wounds, ulcers, burns, natural defects, such as birth defects, and any other defects of biological tissue.

The term "injury" and the like refer to wound or trauma; harm or hurt; usually applied to damage inflicted on the body by an external force.

The phrase "therapeutically effective amount" is used herein to mean an amount sufficient to cause an improvement in a clinically significant condition in the subject, or delays or minimizes or mitigates one or more symptoms associated with the disease or disorder, or results in a desired beneficial change of physiology in the subject.

The term "biocompatible" as used in the application means capable of coexistence with living tissues or organisms without causing harm.

A "polynucleotide" or "nucleotide sequence" is a series of nucleotide bases (also called "nucleotides") in a nucleic acid, such as DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide. This includes single- and double-stranded molecules, I.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates) and with charged linkages (e.g., phosphorothioates, phosphorodithioates). Polynucleotides may contain one or more additional covalently linked moieties, such as, for example, proteins (e.g., nucleases, toxins, antibodies, signal peptides, poly-L-lysine), intercalators (e.g., acridine, psoralen), chelators (e.g., metals, radioactive metals, iron, oxidative metals), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Vectors include, but are not limited to, plasmids, phages, and viruses.

The terms "percent (%) sequence similarity", "percent (%) sequence identity", and the like, generally refer to the degree of identity or correspondence between different nucleotide sequences of nucleic acid molecules or amino acid sequences of proteins that may or may not share a common evolutionary origin. Sequence identity can be determined using any of a number of publicly available sequence comparison algorithms, such as BLAST, FASTA. DNA Strider, or GCG (Genetics Computer Group, Program Manual for the GCG Package, Version 7, Madison, Wis.).

The terms "substantially homologous" or "substantially similar" when at least about 80%, and most preferably at least about 90 or 95%, 96%, 97%, 98%, or 99% of the nucleotides match over the defined length of the DNA sequences, as determined by sequence comparison algorithms, such as BLAST, FASTA, and DNA Strider. An example of such a sequence is an allelic or species variant of the specific genes of the invention. Sequences that are substantially homologous can be identified by comparing the sequences using standard software available in sequence data banks, or in a Southern hybridization experiment under, for example, stringent conditions as defined for that particular system.

The terms "mutant" and "mutation" mean any detectable change in genetic material, e.g. DNA, or any process, mechanism, or result of such a change. This includes gene mutations, in which the structure (e.g. DNA sequence) of a gene is altered, any gene or DNA arising from any mutation process, and any expression product (e.g. protein or enzyme) expressed by a modified gene or DNA sequence. The term "variant" may also be used to indicate a modified or altered gene, DNA sequence, enzyme, cell, etc., i.e., any kind of mutant.

The term "about" or "approximately" means within an acceptable error range for the particular value as determined by one of ordinary skill in the art, which will depend in part on how the value is measured or determined, I.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

As used herein "TNAP" is tissue non-specific alkaline phosphatase, a membrane-bound extracellular glycosylated enzyme capable of changing the ratio of ePPi and ePi. "TNAP" is used to denote the gene encoding the TNAP enzyme.

As used herein, "ANK" or "ANKH" is progressive ankylosis protein, a transmembrane PPi pyrophosphate transporter/channel protein which mediates intracellular to extracellular channeling of PPi that serves to increase ePPi. "Ank1" or "ANK" or "ANKH" is used to denote the gene encoding the ANK or ANKII protein.

As used herein, "ENPP" or "NNP" or "ENPP1" or "PC-ENPP" is plasma cell membrane glycoprotein (PC-1)/ectonucleotide pyrophosphatase/phosphodiesterase-1, an enzyme capable of cleaving extracellular nucleoside triphosphates (eNTP) into ePi or ePPi. "Enpp1" or "ENPP1" or "ENPP" or "Enpp" is used to denote the gene encoding the ENPP protein.

Up-Regulation of TNAP and Down-Regulation of ANK and/or ENPP Leads to Matrix Mineralization in Intervertebral Discs In bone development, the earliest cells that will eventually become the skeleton start out as a cartilage mass that is approximately the shape of the bone to be produced. This cartilage mass is a cartilage matrix with cartilage cells embedded within it. In order to become bone, the cartilage cells must convert their matrix to one that will support bone cells (and bone growth), and then get replaced by bone cells at about the same time that blood vessels invade to deliver a blood supply. This process is well described, and the way in which the cartilage cells modify their matrix is through a process of cell hypertrophy (unknown specific significance) and matrix mineralization. The mineralization of the cartilage matrix is the key modification element that allows the initially (normal) cartilage to be permissive to osteoblast (bone cell) invasion and growth, and thereby able to be converted from mineralized cartilage to bone.

Mobility of the spinal disc is maintained by preserving its mineralization-free state. The inhibition of disc matrix mineralization is poorly understood, but has been suggested to be related to the hypoxia-regulated ANK pyrophosphate transporter (Skubuyte et al. (2010)). Matrix mineralization n general is thought to reflect inorganic phosphate (P) and inorganic pyrophosphate (PPi) ratios, with high Pi/PPi ratios favoring hydroxyapatite (HA) production, as has been shown in vitro (Cheng and Pritzker (1983)). PPi inhibits HA crystal formation, and non-mineralized tissues express enzymes capable of maintaining high extracellular PPi (ePPi) levels (Murshed et al. (2005)).

Three enzymes are consistently reported to control the ePi/ePPi ratio: ANK, PC-1/ENPP, and TNAP. ANK, or progressive ankylosis protein, is a transmembrane PPi pyrophosphate transporter/channel protein that serves to increase ePPi, and when deficient permits non-mineralized tissues to become mineralized through decreased ePPi levels (Gurley el al. (2006)). Plasma cell membrane glycoprotein (PC-1)/ectonucleotide pyrophosphatase/phosphodiesterase-1 (ENPP) is an enzyme capable of cleaving extracellular nucleoside triphosphates (eNTP) into ePi or ePPi, and when deficient similarly correlates with mineralization of typically mineral deficient tissues through decreased ePPi levels (Rutsch et al. (2003); Koshizuka et al. (2001)). Tissue-nonspecific alkaline phosphatase (TNAP) is a membrane-bound extracellular glycosylated enzyme capable of cleaving eNTP or ePPi to change the ratio of ePPi and ePi, and when deficient yields hypomineralized bone as seen in rickets through decreased ePi levels.

From this evidence, it was hypothesized that the spine disc tissue would act similarly if all of these enzymes were present in the tissue, and that what was required was to determine if any of the genes encoding for the three enzymes were missing, such that it could be delivered, and alternatively or additionally, interfere with another gene.

As a model system, a cell culture system of nucleus pulposus (NP) cells derived from cow tail discs was generated (Example 1). Nucleus pulposus cells are "chondrocyte-like cells" that demonstrate the expression of key chondrocyte genes COL2A1, ACAN, and SOX9. There are, however, clear morphologic and physiologic differences between articular cartilage and NP tissues suggesting differences in the cells' phenotypes. For example, hemoglobin chains and carbonic anhydrase 12 are highly expressed in NP cells, likely in order to maintain homeostasis in the avascular hypoxic nutrient deprived, acidic environment of the adult human intervertebral disc (Minogue et al. (2010)). Using real-time PCR for characteristic gene expressions, the NP cultured cells were assessed for Enpp1, Ank1, and TNAP, and were found to express the first two, but not TNAP (Example 1). This was a novel finding.

The human tissue non-specific alkaline phosphatase (TNAP) gene was cloned into a retroviral vector. The recombinant retroviral vector conferred alkaline phosphatase activity to the bovine NP cells (Example 2).

Next a mineralization experiment was performed to determine if gene-delivery of TNAP to the bovine NP cells would confer ability for the recipient cells to mineralize their matrix in monolayer. NP cells mock infected (no virus), infected with a marker gene (LacZ), or infected with TNAP were placed in mineralization media, and assessed at 21 days for matrix mineralization. The novel finding was that in the TNAP infected cells there was obvious mineral deposit in the matrix at 3 weeks (Example 3). However, while the bovine NP cells expressing TNAP were capable of mineralizing matrix in culture, when implanted into a disc culture model from rabbits, a condition more similar to an in vivo environment, no mineralization was observed (Example 4).

This finding lead to an alternative strategy and the further novel finding that the co-treatment of TNAP gene delivery, and reduction in the endogenous expression of Ank1 lead to increased kinetics of mineralization in bovine NP cells in a two-dimensional culture, and conferred the ability of discs to demonstrate mineralization when the TNAP/ANK modified cells were implanted.

Treatment with tumor necrosis factor alpha (TNF-α) of the nucleus pulposus cells caused a reproducible down-regulation of ANK mRNA (Example 10). This effect was hypothesized based upon the finding that the activation of NFκB inhibits ANK (Zhao et al. 2012). The delivery of a short hairpin interfering RNA (shANK) also inhibits ANK mRNA (Example 6).

Either of these ANK suppressing treatments in combination with TNAP expression accelerates the mineralization kinetics of the NP cells (Examples 7 and 9). In addition, gene expression data show that the ENPP gene is down-regulated in the accelerated mineralization condition, as well as the up-regulation of other expected genes (collagen X, runx2) and down-regulation of others (collagen-II, aggrecan) (Example 10).

Implantation of the TNAP/TNF-α cells and TNAP/shANK cells into explanted disc organ culture (rabbit discs) showed "ex vivo" mineralization within the disc in only those conditions, and not significantly in TNAP, TNF-α, shANK, or native cells (Example 11). Without being bound by any theories, these observations led to the hypothesis that mineralization related to the down-regulation of ANKH and ENPP1 and the up-regulation of RUNX2.

Additionally, treatment with interleukin 1β (IL-1β) also caused the enhancement in matrix mineralization (Example 12).

One possible reason for the enhancement is that similar to TNF-α, IL-1β down-regulates ANK. However, the data herein also showed that the gene expression of ENPP was observed to decrease with IL-1β treatment and TNF-α treatment. ANK has been implicated in several studies as an important protein for homeostasis and maintenance of the cell phenotype. There is little published about ENPP besides its role in creating PPi but because it plays a similar role to ANK in regulating PPi it could also regulate the NP niche.

The data indicated ENPP is regulated by IL-1β and the results herein also have shown the gene is responsive to TNF-α as well.

Lastly, additional analysis showed that TNAP/TNF-α infected cells behave most like bone in matrix formation and mineralization (Example 13).

Compositions to Induce Mineralization of Intervertebral Discs

The compositions of the present invention are based upon the surprising discovery that in order for intervertebral discs (IVDs) to mineralize, there needs to be an up-regulation of the expression of TNAP and/or an increase in TNAP, and a down-regulation of the expression of ANK and/or ENPP and/or a decrease in ANK and/or ENPP. Thus, compositions comprising agents that accomplish this gene regulation are contemplated by the invention. Alternatively, agents that increase or promote the activation, amount and/or activity of the TNAP protein, and decrease, prevent or block the activation, amount and/or activity of the ANK and/or ENPP protein can also be part of the composition.

The first component of the composition is an agent that up-regulates or increases expression of TNAP. As shown in the examples, the introduction of the TNAP gene via recombinant/gene therapy techniques accomplishes this increase. Additionally, a nucleic acid which encodes the TNAP protein, or a nucleic acid that is substantially homologous to the TNAP gene, or a variant, mutant, fragment, homologue or derivative of the TNAP gene that produces a protein with maintained or increased function of changing the ratio of ePPi to ePi can also be used in the composition.

The sequence of human and bovine TNAP is available on the National Center for Biotechnology Database and can be used to manufacture variants, mutants, fragments, homologues and derivatives which maintain or have increased function.

One example would be a soluble or diffusible form of TNAP. This form of TNAP has the glycosylphosphatidylinositol anchoring signal eliminated (see, e.g., DiMauro et al. (2002)). Using the soluble form as opposed to the membrane bound TNAP would result less localized mineralization and the ability of the TNAP to diffuse.

Additionally mutants that have increased or accelerated enzyme function have been reported and can also be produced using methods known in the art (see, e.g., DiMauro et al. (2002)). Use of these mutants would increase the effect of the exogenous expression.

While DNA is exemplified, other nucleic acids such as mRNA can also be used.

While a particular retroviral vector, pMX, was exemplified, any vector and delivery system known in the art or later developed could be used to deliver the TNAP gene or mutant, fragment, homologue or derivative to the cells. Viral vectors that are useful in the current invention include but are not limited to retroviral vectors, adeno-associated viruses, oncoretroviral vectors, Herpes simplex virus vector, and lentivirues. Many other eukaryotic and mammalian vectors known in the art and can also be used.

Liposomes are spherical vesicles composed of synthetic lipid bilayers which mimic the structure of biological membranes. The nucleic acid to be transferred is packaged in vitro with the liposomes and used directly for transferring the nucleic acid to a suitable target tissue in vivo. The lipid coating allows the DNA or RNA to survive in vivo, bind to cells and be endocytosed into the cells. Cationic liposomes (where the positive charge on liposomes stabilize binding of negatively charged DNA), are one type of liposome.

The nucleic acids can also be administered with a lipid to increase cellular uptake. The nucleic acids may be administered in combination with a cationic lipid, including but not limited to, lipofectin, DOTMA, DOPE, and DOTAP.

Other lipid or liposomal formulations known in the art can also be used.

Additionally, techniques that deliver nucleic acid without a vector can be used, such as calcium phosphate as described in Krebs et al. (2008), receptor mediated endocytosis, and direct injection/particle bombardment.

The TNAP nucleic acid can be used in the composition in any form that would achieve delivery of the nucleic acid to the composition, e.g., a cell, or to the subject to which the composition is being administered, e.g., a patient.

While it would be understood that any agent or agents that increase or up-regulate the expression of TNAP, would also most likely increase TNAP protein, alternatively, an agent or agents that directly increase or promote the activation, amount and/or activity of the TNAP protein can be used in the composition.

Alternatively, purified TNAP protein can be used in the composition.

TNAP protein can be used in the composition in any form that would achieve delivery of the protein to the composition, e.g., a cell, or to the subject to which the composition is being administered, e.g., a patient.

One such method to deliver TNAP enzyme is the use of mineralizing matrix vesicles to inject into the discs. Mineralizing matrix vesicles (MVs) are extracellular organelles produced by chondrocytes, osteoblasts, and odontoblasts, under physiological conditions, and by vascular smooth muscle cells, under pathological conditions. MVs are involved in the early stage of mineralization allowing calcium and phosphate to accumulate, and therefore providing an optimal environment, facilitating hydroxyapatite formation. MVs are enriched in enzymes controlling Pi and PPi homeostasis (like TNAP). MVs from TNAP-deficient mice are unable to initiate crystals and mineralization (most likely due to excess of PPi). MVs can be isolated and used as described in Buchet et al. (2013). See also Anderson (2003).

The compositions also contain an agent or agents that down-regulate or decrease the expression of ANK and/or ENPP. Some agents, such as tumor necrosis factor-α (TNF-α) and interleukin-1 (IL-1β), down-regulate the expression of both genes. These agents can be incorporated into the composition or can be administered with composition. They can also be used alone or in combination.

TNF-α can be added in an amount ranging from about 1 to 20 ng/ml, with about 5 to 15 ng/ml being preferred, and 10 ng/ml being most preferred.

IL-1β can be added in an amount ranging from about 0.001 to 5 ng/ml, with about 0.01 to 3 ng/ml being preferred, and 2 ng/ml being most preferred.

The cytokine can also be added to the composition by delivery of the gene or RNA encoding the cytokine using the recombinant/gene therapy techniques outlined above and as exemplified in Example 8.

Other cytokines could also be used including but not limited to interleukins (e.g., II.-13), interferons, transforming growth factor (TGF), epidermal growth factor (EGF), insulin growth factor (IGF), fibroblast growth factor (FGF), vascular endothelial growth factor (VEGF), dermal growth factor, stem cell factor (SCF), granulocyte-colony stimulating factor (G-CSF), granulocyte-macrophage stimulating factor (GM-CSF), stromal cell-derived factor-1, steel factor, platelet derived growth factor (PDGF), angiopoietins (Ang), hepatocyte growth factor, insulin-like growth factor (IGF-1), colony-stimulating factors, thrombopoietin, erythropoietin, fit3-ligand, nerve growth factor (NGF), and substance P, as well as combinations thereof.

Other agents can be used to down-regulate ANK and/or ENPP. Such agents include but are not limited to chemicals, phytochemicals, pharmaceuticals, biologics, inorganic molecules, small organic molecules, antibodies, nucleic acids, peptides, and proteins. Some of these agents can be designed using the sequences of ANK and ENPP which are both publicly available in the National Center for Biotechnology Database.

Examples of such agents are hypoxia-inducible factor (HIF) proteins, 1 and 2. These proteins have been found to bind to particular motifs on the ANK gene promoter, HRE-1 and HRE-2 (Skubutyle et al. (2010)). Additionally, small molecules that bind to these motifs in the ANK gene can be designed by methods known in the art using the sequence of the ANK gene.

RNA interference or RNAi refers to the ability of double stranded RNA (dsRNA) to suppress the expression of a specific gene of interest in a homology-dependent manner. RNA interference commonly involves the use of dsRNAs that are greater than 500 bp, however, it can also be mediated through small interfering RNAs (siRNAs) or small hairpin RNAs (shRNAs), which can be 10 or more nucleotides in length and are typically greater than 18 nucleotides in length, around 20-25 base pairs in length.

These RNAi can also be used to down-regulate the expression of ANK and ENPP, especially siRNA and shRNA. A siRNA and shRNA for ANK is exemplified in Example 5, but siRNA can designed by methods known in the art using the sequence of the ANK and ENPP mRNA.

MicroRNA can also be used to down-regulate ANK and/or ENPP expression. MicroRNAs are small non-coding RNAs averaging 22 nucleotides that regulate the expression of their target mRNA transcripts by binding. (Ambros (2004); Bartel (2009)). Binding of microRNAs to their targets is specified by complementary base pairing between positions 2-8 of the microRNA and the target 3' untranslated region (3' UTR), an mRNA component that influences translation, stability and localization (Bartel (2009)). Again microRNAs that bind to the 3'UTR of the ANK or ENPP mRNA can designed by methods known in the art using the sequence of the ANK and ENPP mRNA.

Agents that decrease, prevent or block the activation, amount and/or activity of the ANK and/or ENPP enzymes can also be used. Agents that inhibit ANK include but are not limited to probenecid (Zhao et al. (2012)), used in patients to prevent gout and gouty arthritis. Agents that inhibit ENPP include but are not limited to pyridoxal-phosphate-6-azophenyl-2',4'-disulfonate (PPADS), and the nonspecific ectonucleotidase antagonist, 6-N,N-diethyl-β-γ-dibromo methylene-DI-adenosine 5-triphosphate (ARL 67156).

These agents would include antibodies to ANK and/or ENPP enzyme including antibodies to the active sites of these enzymes.

The terms "antibody" and "antibodies" include polyclonal antibodies, monoclonal antibodies, humanized or chimeric antibodies, single chain Fv antibody fragments, Fab fragments, and F(ab')$_2$ fragments. Polyclonal antibodies are heterogeneous populations of antibody molecules that are specific for a particular antigen, while monoclonal antibodies are homogeneous populations of antibodies to a particular epitope contained within an antigen. Monoclonal antibodies and humanized antibodies are particularly useful in the present invention.

Antibody fragments that have specific binding affinity for a target of interest can be generated by known techniques. Such antibody fragments include, but are not limited to, F(ab')$_2$ fragments that can be produced by pepsin digestion of an antibody molecule, and Fab fragments that can be generated by reducing the disulfide bridges of F(ab')$_2$ fragments. Alternatively, Fab expression libraries can be constructed. Single chain Fv antibody fragments are formed by linking the heavy and light chain fragments of the Fv region via an amino acid bridge (e.g., 15 to 18 amino acids), resulting in a single chain polypeptide. Single chain Fv antibody fragments recognizing a target of interest can be produced through standard techniques, such as those disclosed in U.S. Pat. No. 4,946,778.

Inhibiting the enzymes can also be effected using "decoy" molecules which mimic the region of a target molecule to which ANK and/or ENPP binds and activates. The ANK and/or ENPP enzyme would bind to the decoy instead of the target, and activation could not occur.

Inhibition can also be effected by the use of a "dominantly interfering" molecule, or one in which the binding portion of ANK and/or ENPP is retained but the molecule is truncated so that the activating domain is lacking. These molecules would bind but be unproductive and block the native ANK and ENPP enzymes from binding. Such decoy molecules and dominantly interfering molecule can be manufactured by methods known in the art.

In one embodiment, the composition comprises an agent or agents that increase or up-regulate the expression of TNAP and an agent or agents that decrease or down-regulate the expression of ANK. In an alternative embodiment, the composition comprises an agent or agents that increase or up-regulate the expression of TNAP and an agent or agents that decrease or down-regulate the expression of ENPP. In a further embodiment, the composition comprises an agent or agents that increase or up-regulate the expression of TNAP and an agent or agents that decrease or down-regulate the expression of ANK, and an agent or agents that decrease or down-regulate the expression of ENPP. It should be noted in some cases, a single agent can down-regulate the expression of both ANK and ENPP. In all of these embodiments, an agent or agents that increase or promote the activation, amount and/or activity of the TNAP protein and an agent or agents that decrease, prevent or block the activation, amount and/or activity of the ANK and/or ENPP enzyme can also be used.

The composition can also comprise other agents that facilitate migration, integration, regeneration, proliferation, and growth of cells into and around the injury or defect, and/or promote healing of the injury or defect, and/or are osteogenic, i.e., build, grow and produce bone.

These agents, include but are not limited to, cytokines, chemokines, chemoattractants, anti-microbials, anti-virals, anti-inflammatories, bone regenerator molecules, anti-immune agents, and combinations thereof.

The composition can also comprise other agents that promote osteogenic growth including but not limited to bone morphogenetic proteins, BMP binding proteins, transforming growth factor-beta (TGF-β) family members, TGF-1, WNT family members, epidermal growth factor (EGF), NELL-1, LIM mineralization protein-1, and noggin inhibitors.

Cytokines for use in the invention include, but are not limited to, interleukins (e.g., IL-13), interferons, transforming growth factor (TGF), epidermal growth factor (EGF), insulin growth factor (IGF), fibroblast growth factor (FGF), vascular endothelial growth factor (VEGF), dermal growth factor, stem cell factor (SCF), granulocyte-colony stimulating factor (G-CSF), granulocyte-macrophage stimulating factor (GM-CSF), stromal cell-derived factor-1, steel factor, platelet derived growth factor (PDGF), angiopoietins (Ang), hepatocyte growth factor, insulin-like growth factor (IGF-1), colony-stimulating factors, thrombopoietin, erythropoietin, fit3-ligand, nerve growth factor (NGF) and substance P, as well as combinations thereof.

Chemokines include, but are not limited to, CC, CXC, C, and $CX_3C$ chemokines.

Chemoattractants include, but are not limited to, bone morphogenic protein (BMP), fibroblast growth factor (FGF), and transforming growth factor (TGF).

Anti-microbial agents include, but are not limited to, 3-lactam antibiotics, such as cefoxitin, n-formamidoyl thienamycin and other thienamycin derivatives, tetracyclines, chloramphenicol, neomycin, gramicidin, bacitracin, sulfonamides, aminoglycoside antibiotics such as gentamycin, kanamycin, amikacin, sisomicin and tobramycin, nalidixic acids and analogs such as norfloxican, the antimicrobial combination of fluoroalanine/pentizidone, and nitrofurazones.

Anti-inflammatory agents, that inhibit or prevent an immune response in vivo, can also be added to the composition. Exemplary anti-inflammatory agents include: agents which inhibit leukocyte migration into the area of injury ("leukocyte migration preventing agents"); and antihistamines. Representative leukocyte migration preventing agents include, but are not limited to, silver sulfadiazine, acetylsalicylic acid, indomethacin, and Nafazatrom. Representative anti-histamines include, but are not limited to, pyrilamine, chlorpheniramine, tetrahydrozoline, antazoline, and other anti-inflammatories such as cortisone, hydrocortisone, beta-methasone, dexamethasone, fluocortolone, prednisolone, triamcinolone, indomethacin, sulindac, its salts and its corresponding sulfide.

One form of the composition are cells comprising agents that increase or up-regulate TNAP and/or that increase or promote the activation, amount and/or activity of the TNAP protein and decrease or down-regulate ANK and/or ENPP and/or decrease, prevent or block the activity, amount, and/or activation of the ANK and/or ENPP enzyme. The cells can be prokaryotic, or eukaryotic, including mammalian cells, and nucleus pulposus cells.

The nucleus pulposus cells can be from any mammal. Human and bovine are most preferred.

It has been discovered that bovine nucleus pulposus cells, treated with agents that up-regulate the expression of TNAP and down-regulate the expression of ANK and/or ENPP, mineralize. When administered to spinal discs, the cells induce matrix mineralization in the discs.

Because the intervertebral disc space does not have its own blood supply and no arteries or capillaries, only very small molecules can pass in and out. The immune response in IVDs is very slow such that any foreign material will be cleared before it can cause an unwanted immune response. Thus, the use of a xenograft, e.g., bovine cells injected into a human, has few immediate immunological consequences.

In a further embodiment, the cell is from a human and is an allograft. In another embodiment the cell is autograft. In either of these embodiments, the cells are harvested from the human by methods known in the art, cultured, and administered or infected with an agent or agents that increase or up-regulate the expression of TNAP and/or that increase or promote the activation, amount and/or activity of the TNAP protein and decrease or down-regulate ANK and/or ENPP and/or decrease, prevent or block the activity, amount, and/or activation of the ANK and/or ENPP enzyme, and then implanted back into the IVD. Cells that can be used in this embodiment include but are not limited to nucleus pulposus cells, cartilage cells, and bone marrow cells.

Thus, one embodiment of the present invention is a composition in the form of, or comprising a cell, further comprising an agent or agents that increase or up-regulate the expression of TNAP and/or that increase or promote the activation, amount and/or activity of the TNAP protein and decrease or down-regulate ANK and/or ENPP and/or decrease, prevent or block the activity, amount, and/or activation of the ANK and/or ENPP enzyme.

The cell can be prokaryotic or eukaryotic, and in a further embodiment, the cell is a mammalian cell. In a further embodiment, the cell is a bovine cell. In yet another embodiment, the cell is human. In a further embodiment, the cells are non-pathogenic bacteria.

Cells that can be used include but are not limited to bone marrow, cartilage cells, and nucleus pulposus cells.

Another embodiment of the present invention is a cell culture comprising cells comprising an agent or agents that increase or up-regulate the expression of TNAP and/or that increase or promote the activation, amount and/or activity of the TNAP protein and decrease or down-regulate ANK and/or ENPP and/or decrease, prevent or block the activity, amount, and/or activation of the ANK and/or ENPP enzyme. The cell culture can comprise prokaryotic or eukaryotic cells. The cell culture can be mammalian, preferably bovine or human cells.

The amount of cells to be delivered or administered to a subject can be determined by the clinician or person of skill in the art but generally the cells can delivered or administered in an amount ranging from about $1\times10^6$ to about $1\times10^9$, or ranging from about $1\times10^6$ to about $1\times10^8$, or ranging from about $1\times10^6$ to about $1\times10^7$. The cells will usually need to be concentrated in order to deliver a large number of cells to the small volume of an IVD. Cells can be concentrated from the cell culture by any method known in the art including centrifugation. The cells can purified from the culture medium or they can remain in the culture medium.

In yet another embodiment the composition can comprise an agent or agents that increase or up-regulate the expression of TNAP and/or that increase or promote the activation, amount and/or activity of the TNAP protein and decrease or down-regulate ANK and/or ENPP and/or decrease, prevent or block the activity, amount, and/or activation of the ANK and/or ENPP enzyme, in a pharmaceutical preparation. The pharmaceutical preparation can be prepared using any pharmaceutically acceptable carrier or excipient. The phrase "pharmaceutically acceptable" refers to molecular entities and compositions that are physiologically tolerable and do not typically produce an allergic or similar untoward reaction, such as gastric upset, dizziness and the like, when administered to a human, and approved by a regulatory agency of the Federal or a state government or listed in the U.S. Pharmacopeia or other generally recognized pharmacopeia for use in animals, and more particularly in humans. "Carrier" refers to a diluent, adjuvant, excipient, or vehicle with which the therapeutic is administered. Such pharmaceutical carriers can be sterile liquids, such as saline solutions in water and oils, including those of petroleum, animal, vegetable, or synthetic origin, such as peanut oil, soybean oil, mineral oil, sesame oil, and the like. Saline solutions and aqueous dextrose and glycerol solutions can also be employed as liquid carriers, particularly for injectable solutions.

The preferred form of pharmaceutical preparation is one for delivery by injection into the IVD. Extemporaneous injection solutions and suspensions may be prepared from sterile powders, granules, and tablets. Suitable vehicles that can be used to provide parenteral dosage forms of the invention are well known to those skilled in the art. Examples include: Water for Injection USP; aqueous vehicles such as Sodium Chloride Injection, Ringer's Injection, Dextrose Injection, Dextrose and Sodium Chloride Injection, and Lactated Ringer's Injection; water-miscible vehicles such as ethyl alcohol, polyethylene glycol, and polypropylene glycol; and non-aqueous vehicles such as corn oil, cottonseed oil, peanut oil, sesame oil, ethyl oleate, isopropyl myristate, and benzyl benzoate.

A further embodiment of the present invention are cells comprising an agent or agents that increase or up-regulate the expression of TNAP and/or that increase or promote the activation, amount and/or activity of the TNAP protein and decrease or down-regulate ANK and/or ENPP and/or decrease, prevent or block the activity, amount, and/or activation of the ANK and/or ENPP enzyme, in a pharmaceutical preparation as described above.

Yet another embodiment of the present invention is a culture of cells comprising an agent or agents that increase or up-regulate the expression of TNAP and/or that increase or promote the activation, amount and/or activity of the TNAP protein and decrease or down-regulate ANK and/or ENPP and/or decrease, prevent or block the activity, amount, and/or activation of the ANK and/or ENPP enzyme, in a pharmaceutical preparation as described above.

Methods of Use of the Composition

The composition of the present invention can be used in a method to activate and/or promote mineralization of biological tissue, especially intervertebral discs, by administering the composition into a subject in need thereof.

The composition can also be used in a method to fuse two contiguous vertebrae by administering the composition of the present invention into the intervertebral disc between the two vertebrae in a subject in need thereof.

The composition can also be used in a method to treat, repair and/or replace defects and/or injuries to biological tissue, more specifically intervertebral discs, by administering the composition into a subject in need thereof.

Those of skill in the art would appreciate that the composition of the present invention may be administered to a subject using operative techniques and procedures, utilizing such techniques as magnetic resonance imaging and computer guided technology.

Figure 1A:
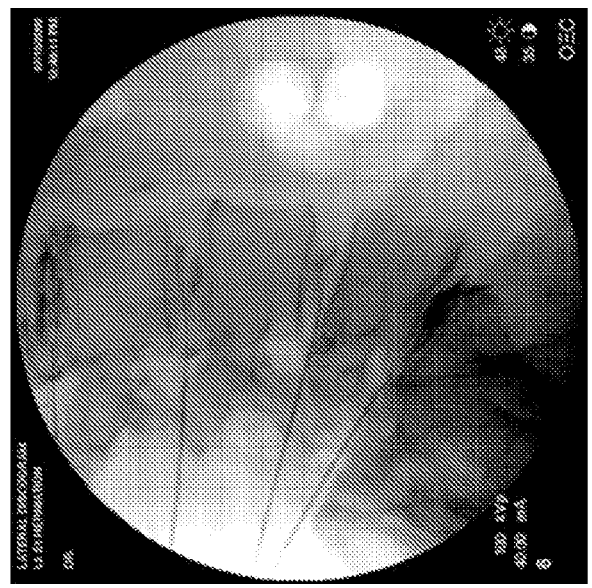

A preferred method of administration of the compositions for use in the methods discussed above is percutaneous injection through the annulus fibrosus into the nucleus pulposus tissue of the IVD as shown in FIG. 1A. When the composition is administered in this way to the IVD, the IVD mineralizes and becomes bone. This bone then bridges and fuses the two vertebrae on each side of the IVD as shown in FIG. 1B.

While both anterior and posterior fusion can be performed, anterior spine fusion is preferred because it is mechanically more stable, has a larger area for fusion, and has a natural containment for bone production in the annulus fibrosus (FIG. 1A).

One such technique for delivering compositions into the disc is discography percutaneous (fluoroscopy guided) technique. This method is currently used by clinicians mostly as a diagnostic but sometimes as a treatment, using dye or saline as the injectate. In this technique, as illustrated in FIG. 1A, percutaneous access to the disk is provided by injection. While this technique is currently in clinical use, it will be understood that the current invention is to the composition injected or otherwise placed, implanted or administered into the spine or other body part, and any delivery method, known or developed in the future, that accomplishes this goal can be used with the composition of the present invention to promote mineralization of the IVDs or other biological tissue, or to fuse two or more vertebrae, or to treat, repair and/or replace defects and/or injuries to biological tissue, more specifically intervertebral discs.

Additionally, other tissue that would be in need of mineralization but does not mineralize in nature could be activated or promoted to mineralize using the compositions of the present invention. For example, the compositions of the present invention could be injected into a small joint, such as a finger or toe, or a large joint, such as a knee, shoulder or hip, especially in patients who are too sick or disabled to tolerate standard treatments.

Kits

The present invention also includes kits for mineralizing biological tissue, especially intervertebral discs, and/or performing the fusion of two or more vertebrae, i.e., spine fusion. Such kits could include the compositions of the present invention, a tool or tools for administration, e.g., a syringe for injection, and instructions for use, including determining the correct amount of composition to be administered, and the placement of the administration, e.g., injection.

Drug Screening and Research Tools

The compositions of the present invention, in particular the bovine NP cells exemplified in Example 1 which do not express TNAP, can be used for drug screening for potential therapeutics for both spine fusion and mineralization defects, and research tools.

For this method, a test agent is contacted or administered to the NP cells and the cells are then tested for a change in phenotype, in particular the ability to mineralize. Cells that were contacted or administered the test agent could also be analyzed for gene expression, in particular of the expression of TNAP, ANK and ENPP. Test agents that allowed cells to mineralize and/or up-regulated TNAP and/or down-regulated ANK and/or ENPP, would be considered potential therapeutics for spine fusion and mineralization defects.

NP cells that have already comprise agents that up-regulate TNAP and/or down-regulate ANK and/or ENPP can also be used for drug screening using the method outlined above. These cells can be contacted with or administered a test agent, and then tested for a change in phenotype, in particular the enhanced mineralization of these cells. These cells could also be analyzed for the expression of NAP, ANK and ENPP. Again, test agents that up-regulated TNAP and/or down-regulated ANK and/or ENPP, as compared to baseline expression of these genes in these cells, would be considered potential therapeutics for spine fusion and mineralization defects.

The term "test agent" is used in the same ways as "agent" and means a substance that produces or is capable of producing an effect and would include, but is not limited to, chemicals, pharmaceuticals, biologics, small organic molecules, antibodies, nucleic acids, peptides, and proteins.

All of the exemplified NP cells can be used as basic research tools. For example, analysis of the expression of additional genes could be performed on any of these cells to gain a better understanding of the mechanisms of mineralization. Additionally, gene expression profiles of the native NP cells lacking TNAP can be compared to those cells infected with TNAP and to those co-infected with TNAP and TNF-α or IL-1β, or another agent that down-regulates ANK and/or ENPP.

EXAMPLES

The present invention may be better understood by reference to the following non-limiting examples, which are presented in order to more fully illustrate the preferred embodiments of the invention. They should in no way be construed to limit the broad scope of the invention Example 1—Bovine NP Cells Lack TNAP Materials and Methods Freshly butchered bovine tails are commercially available, and were used to obtain primary NP tissue.

Spinal discs were axial sectioned, the gelatinous NP was removed from the disc space, collagenase (0.5%) treated with shaking overnight, washed and strained (40 μM pore), and plated in high glucose DMEM with 10% fetal bovine serum on tissue culture plastic. Preparation for bovine caudal disc culture required separation of the disc from the spine by disrupting the cartilage endplate from the bone endplate on each side of the disc. The entire disc from cartilage endplate to endplate was then cultured in 50 mL Falcon tubes in DMEM/10% FBS.

Hypoxic culture conditions were created with a hypoxia chamber maintained within a dedicated incubator, with compressed nitrogen (T. W. Smith) displacing the gas within the chamber until the oxygen sensor detects that oxygen levels fall below the set level (1%). Since carbon dioxide was also eliminated from the chamber, HEPES buffer was used to control pH in the media.

The tissue monolayer cultures of NP cells were characterized for gene expression for collagen II (COL2A1), aggregan (ACAN), cytokeratin 18 (KRT18), sex-determining region Y, box9 (SOX9), versican (VCAN) as well as ENPP, ANK, and TNAP using qualitative polymerase chain reaction (Qiagen and Biorad).

Results

Figure 2:
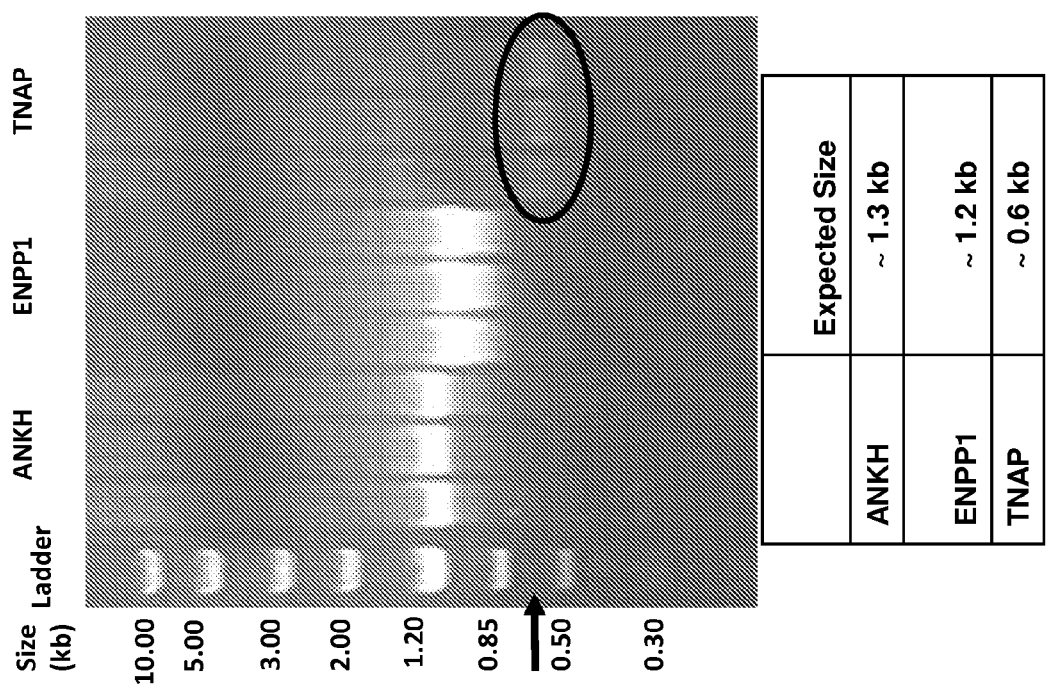
FIG. 2 is a gel showing the results of polymerase chain reaction and the expression of ANKH, ENPP1 and TNAP in bovine nucleus pulposus cells.
Figure 3:
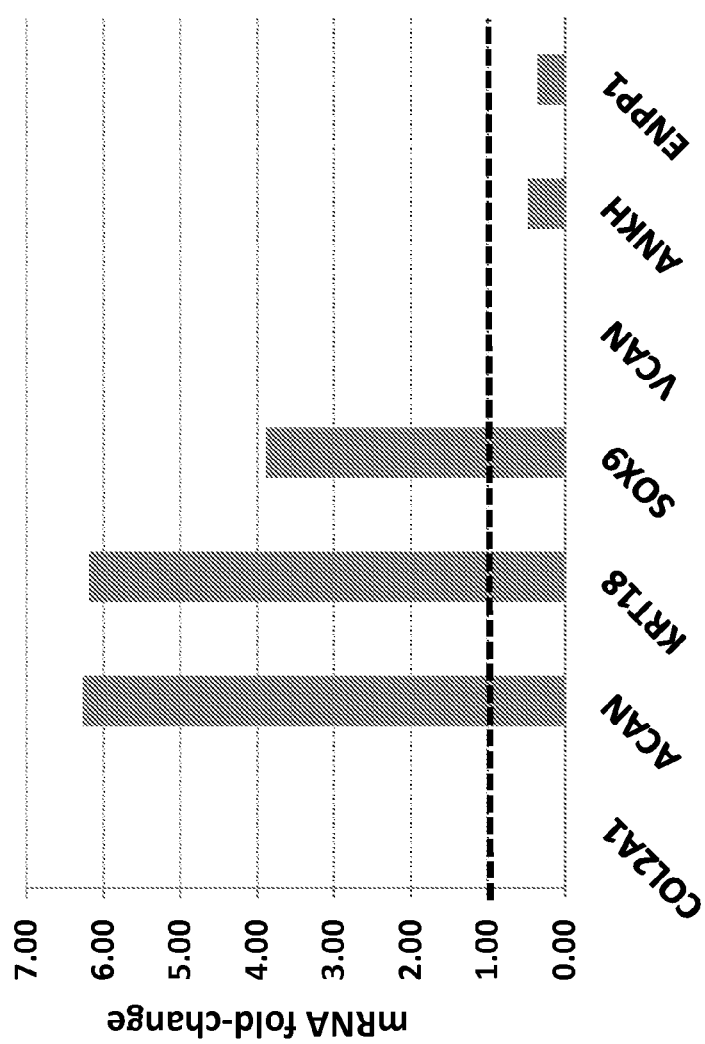
FIG. 3 is a graph showing the results of polymerase chain reaction showing the relative expression of genes in bovine NP cells incubated under hypoxic conditions (1%) oxygen, as compared to normal condition (21% oxygen). Dashed line indicates gene expression under normal conditions.

The tissue monolayer cultures of NP derived from bovine caudal discs were found to be consistent with NP cells through gene expression, including collagen-II, aggrecan, and cytokeratin 18. The bovine NP cells expressed ENPP and ANK, but did not express TNAP (FIG. 2). Results also showed that culture of the NP cells in a level of hypoxia that would reflect the typical levels observed in the disc (1% oxygen vs 21%) led to decreased ANK message levels, along with decreased message levels for ENPP, COL2A1, and VCAN and increased expression of ACAN, KRT18, and SOX9 (FIG. 3).

Example 2—Over-Expression of TNAP Using a Retroviral Vector

Materials and Methods

Bovine NP cells were obtained and cultured as described in Example 1 except DMEM, with 5% FBS, lx antibiotic-antimycotic, and 10 &M HEPES (Gibco) was used. Passage 2 cells were transduced.

A human tissue non-specific alkaline phosphatase (TNAP) gene was purchased from a commercial vendor through NCBI (Open Biosystems). The hTNAP was cloned into a retroviral vector, pMX-ires-bsr. The resulting recombinant provirus was packaged with Phoenix cells and was used to transduce the bovine cells by spinoculation. Selection was done using 4 μ/ml of blasticidin. LacZ in the pMX-ires-bsr was used as a control vector and showed that the infection with the retroviral vector was efficient.

TNAP mRNA was measured using qualitative polymerase chain reaction. Total RNA was isolated from the bovine NP cultures. Amplifications were carried out using primers specific for TNAP. Data were calculated as the ratio of TNAP to a housekeeping gene compared to a reference sample. Protein levels were measured by alkaline phosphatase activity staining of fixed culture specimens.

Results

Figure 4:
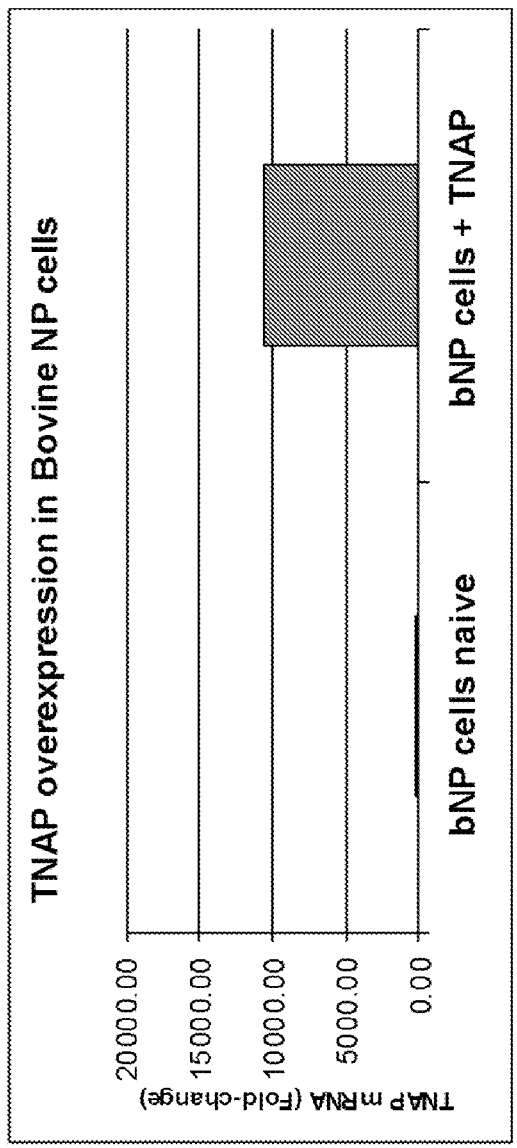
FIG. 4 is a graph depicting the results of polymerase chain reaction for the expression of TNAP mRNA on naïve BNP cells and BNP cells infected with TNAP.

As shown in FIG. 4, the NP cells infected with the TNAP retroviral vector overexpressed TNAP by about 1000 fold over naïve bovine NP cells.

Figure 5B:
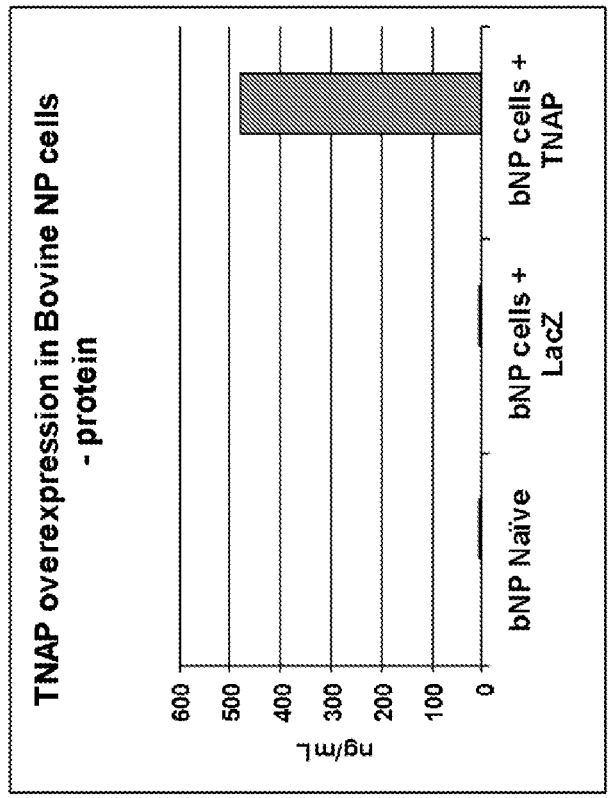
FIG. 5B shows a graph of results of alkaline phosphatase activity in naïve BNP cells, BNP cells infected with LacZ, and BNP cells infected with TNAP.
Figure 5A:
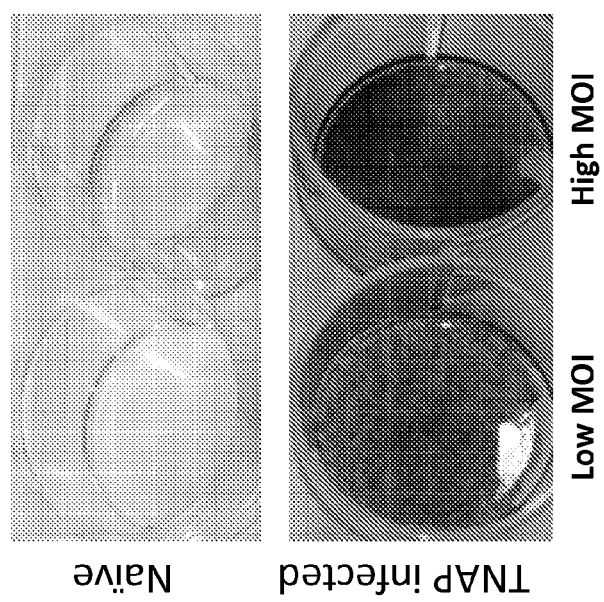
FIG. 5A shows images of naïve BNP cells and BNP cells infected with TNAP stained with alkaline phosphatase stain.

Moreover, the over-expression of TNAP led to an increase in alkaline phosphatase activity. Cells infected with TNAP retroviral vector had significantly higher AP activity as compared to naive bovine NP cells and those infected with the retroviral vector and LacZ (FIGS. 5A and 5B).

Example 3—Over-Expression of TNAP in Bovine NP Cells Leads to Matrix Mineralization Materials and Methods The cells from Example 2 (TNAP infected, LacZ infected, and naïve) were grown in high density cultures in a medium comprising DMEM high glucose (4.5 g/L) plus 1% Pen-Strep, and 10% FBS (normal medium). Some cells were grown in medium additionally containing 50 μ/ml ascorbic acid (Sigma-Aldrich), and 5 mM of β-glycerophosphate (Sigma-Aldrich) ("mineralization medium"). Medium was changed every three days. Cells were grown under normal and hypoxic culture conditions as described in Example 1.

After 21 days (three weeks), the cells were stained with Alizarin Red (Sigma-Aldrich) as described in Gregory et al. (2004). Briefly, plates were fixed, rinsed, stained, imaged and the staining quantified after acetic acid dissolution on a photospectrometer. von Kossa staining was also performed.

Results

Figure 6B:
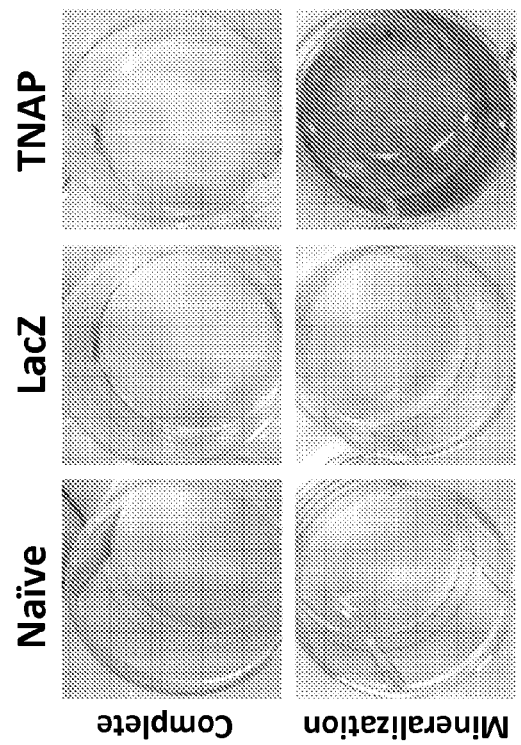
FIG. 6A shows images of Alizarin Red staining, and FIG. 6B, Von Kossa staining, of naïve BNP cells, BNP cells infected with LacZ, and BNP cells infected with TNAP in complete medium and mineralization medium.
Figure 6A:
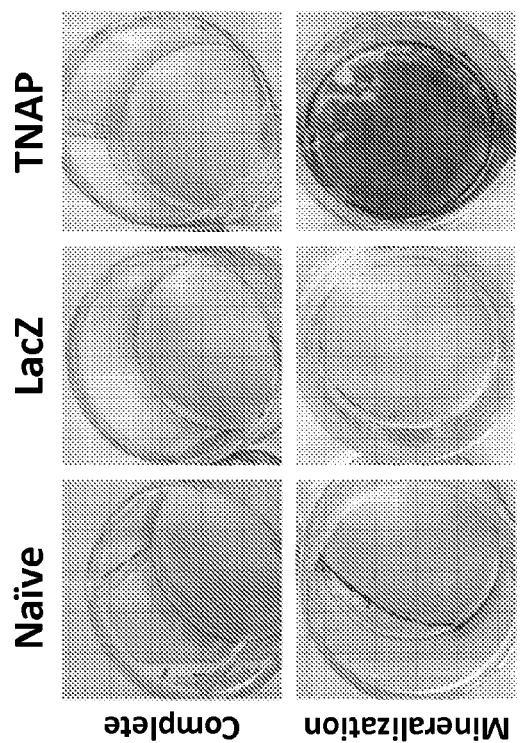

As shown in FIGS. 6A and B, after 21 days the only cell cultures showing mineralization via Alizarin Red and Von Kossa staining were the TNAP infected bovine NP cells in the presence of ascorbic acid and -glycerophosphate, i.e., mineralization medium.

Thus, the over-expression of TNAP in bovine NP cells led to matrix mineralization in a monolayer in the presence of ascorbic acid and -glycerophosphate.

Example 4—Over-Expression of TNAP Alone does not Lead to Matrix Mineralization in Discs Materials and Methods New Zealand white rabbits were euthanized and the spines harvested. The vertebral bodies were fractured to isolate the intervertebral discs. The discs were cultured in high glucose DMEM as described in Example 3 for four weeks. The cells maintained high viability over this time period.

The discs were then injected with the cells from Example 2 (TNAP infected, LacZ infected, and naïve) and the discs were incubated for four weeks and then analyzed for mineralization by x-ray and microCT to quantify mineralization.

Results

Figure 7A:
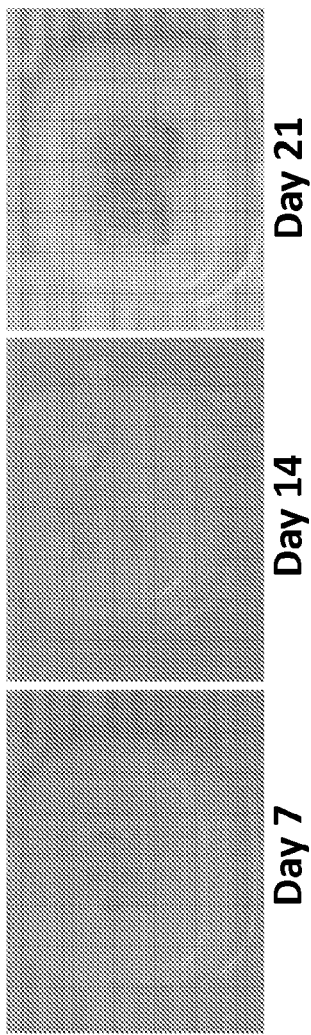
FIG. 7A is x-gal staining of rabbit disc injected with BNP cells infected with TNAP at 7, 14, and 21 days.

As shown in FIG. 7A, the LacZ infected cells from Example 2 injected into the rabbit discs were viable and produced B-gal as noted by the staining, for up to three weeks in culture.

Figure 7B:
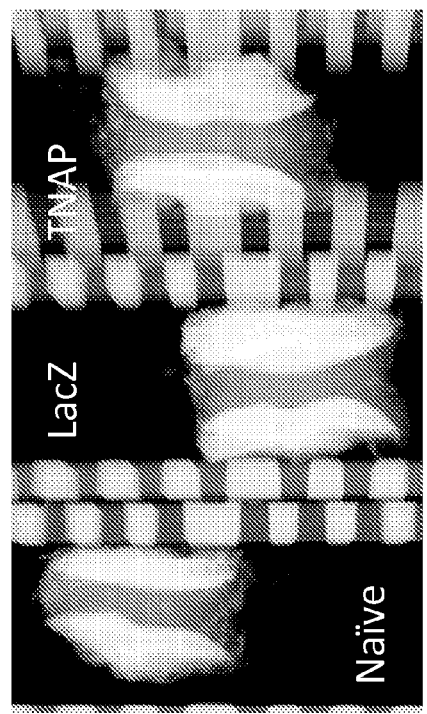
FIG. 7B are x-ray images of rabbit discs injected with naïve BNP cells, BNP cells infected with LacZ, and BNP cells infected with TNAP.

The x-ray images in FIG. 7B showed there was no increase in bone formation in the disc injected with TNAP infected cells as compared to naïve or LacZ infected cells.

These results were in agreement with microCT results (Table 1) in that there was no increase bone volume in disks injected with cells infected with TNAP as compared to LacZ infected and naïve. There was also no change in total volume between the three groups.

TABLE 1

Bone Volume as Measured by microCT in Rabbit Discs injected with Bovine NP Cells Infected with TNAP

| DISC # | Cells Infected | TV | BV | BV/TV |
|---|---|---|---|---|
| 1 | TNAP | 94.79 | 0.001 | 0.000 |
| 2 | TNAP | 132.85 | 0.000 | 0.000 |
| 3 | TNAP | 117.44 | 0.000 | 0.000 |
| 4 | TNAP | 81.78 | 0.000 | 0.000 |
| 5 | TNAP | 83.47 | 0.000 | 0.000 |
| 6 | TNAP | 96.98 | 0.000 | 0.000 |
| 7 | TNAP | 123.02 | 0.000 | 0.000 |
| 8 | LacZ | 87.43 | 0.000 | 0.000 |
| 9 | LacZ | 96.68 | 0.000 | 0.000 |
| 10 | LacZ | 95.21 | 0.001 | 0.000 |
| 11 | LacZ | 98.44 | 0.000 | 0.000 |
| 12 | LacZ | 129.27 | 0.000 | 0.000 |
| 13 | LacZ | 98.74 | 0.0002 | 0.000 |
| 14 | Naïve | 76.60 | 0.004 | 0.000 |
| 15 | Naïve | 120.14 | 0.000 | 0.000 |
| 16 | Naïve | 106.52 | 0.000 | 0.000 |
| 17 | Naïve | 103.10 | 0.000 | 0.000 |

TV—total volume (disc)
BV—Bone volume (mineral formed)

Example 5—Cloning Short Hairpin Interfering RNA of ANKH

Materials and Methods

The sequence of the bovine ANK gene was obtained from the NCBI database, which has 91% homology with human ANK, and the method of Baroy et al. was used to generate the siRNA. Briefly, total RNA was harvested from the bovine NP cells, cDNA prepared, and nested PCR primers designed from the sequence were used to generate specific zonal cassettes to be cloned. Multiple clones were made and assessed for the ability to knock out the ANK gene in tissue culture following transient expression.

Figure 8:
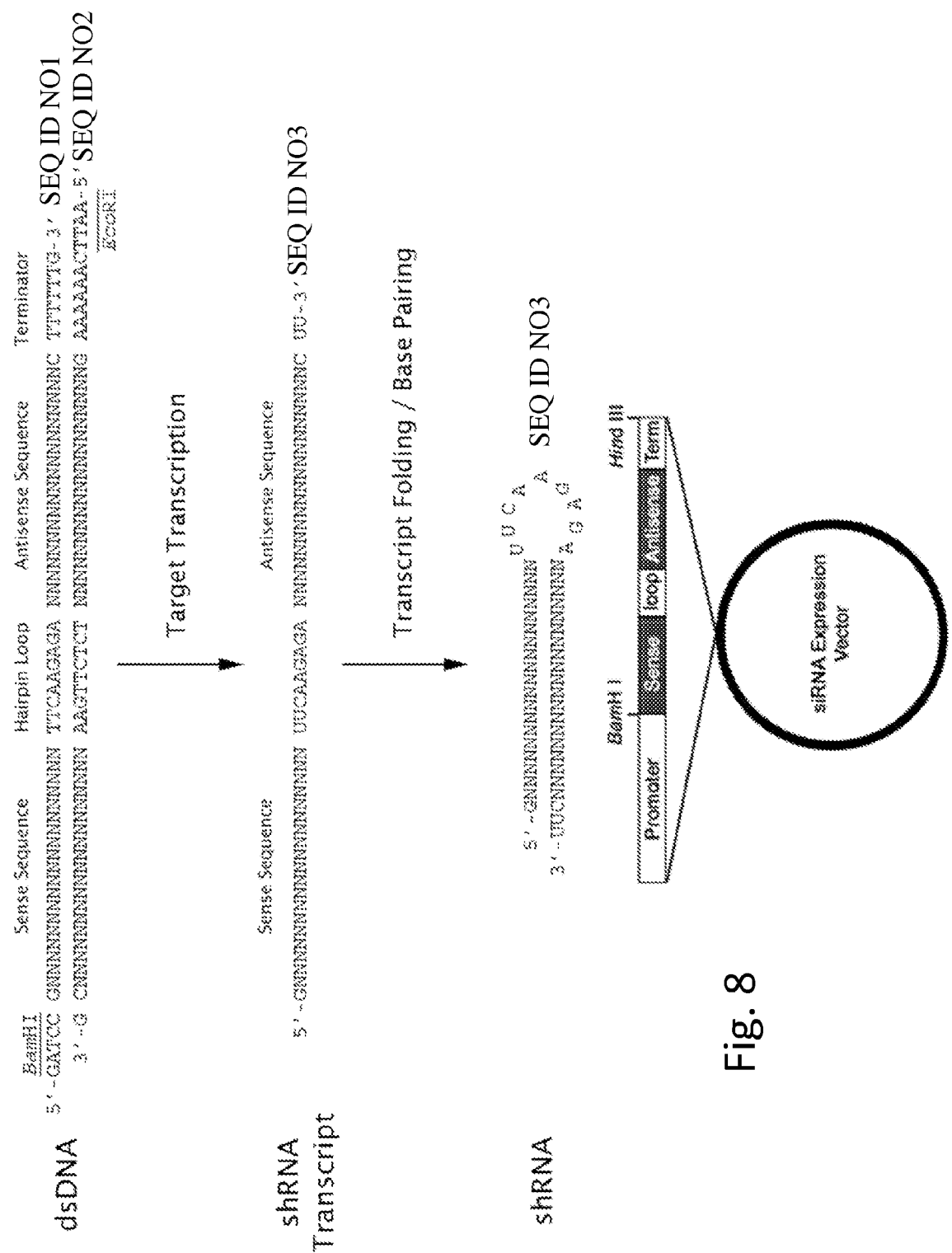
FIG. 8 is a schematic of the production of the shANKH RNA.

The most successful siRNA construct was converted into a short hairpin RNA (shRNA) and cloned into an RNA expression vector. A schematic of the cloning of the shANKH is shown in FIG. 8.

Example 6-Knocking Down of ANKH Using a Retroviral Vector Containing shANKII

Materials and Method

Bovine NP cells described in Example 2 were transduced by spinoculation with both the shANKH knock down vector described in Example 5 and the pMXs-IRES-bsr-TNAP construct described in Example 2 to obtain a double infected cell. Selection was performed using blasticidin and puromycin, and LacZ was used as a control.

ANKH mRNA was measured using qPCR under normal conditions and hypoxic as described in Example 2.

Results

Figure 9:
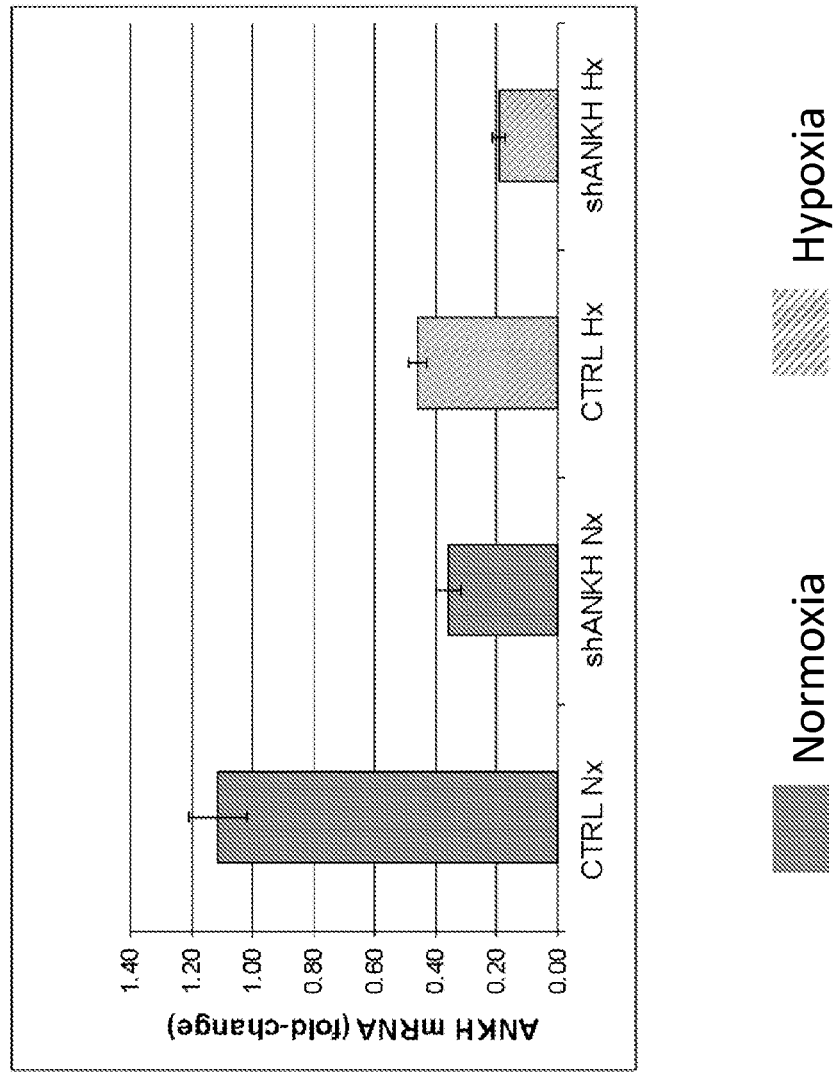
FIG. 9 is a graph depicting results of polymerase chain reaction under normal conditions (solid bars on the left hand side of the graph labeled "Nx") and hypoxic conditions (hashed bars on the right side of the graph labeled "Hx") for the expression of ANKH mRNA on BNP cells infected with LacZ (labeled "CTRL") and BNP cells infected with shANKII (labeled "shANKH").

Bovine NP cells infected with the knock down vector showed a significant decrease in ANKH mRNA expression as compared to controls in both normal and hypoxic conditions (FIG. 9).

Example 7—Effect of TNF-α on Mineralization

Materials and Methods

The cells from Example 2 (TNAP infected and naïve) were grown in high density cultures in a medium comprising DMEM high glucose (4.5 g/L) plus 1% PenStrep, and 10% FBS, and 50 µ/ml ascorbic acid, and 5 mM of β-glycerophosphate (mineralization medium). Some cells were also stimulated with 10 ng/mL of hfTNF-α.

The cells were stained with Alizarin Red and von Kossa stain after 7, 14, and 21 days.

Results

Figure 10:
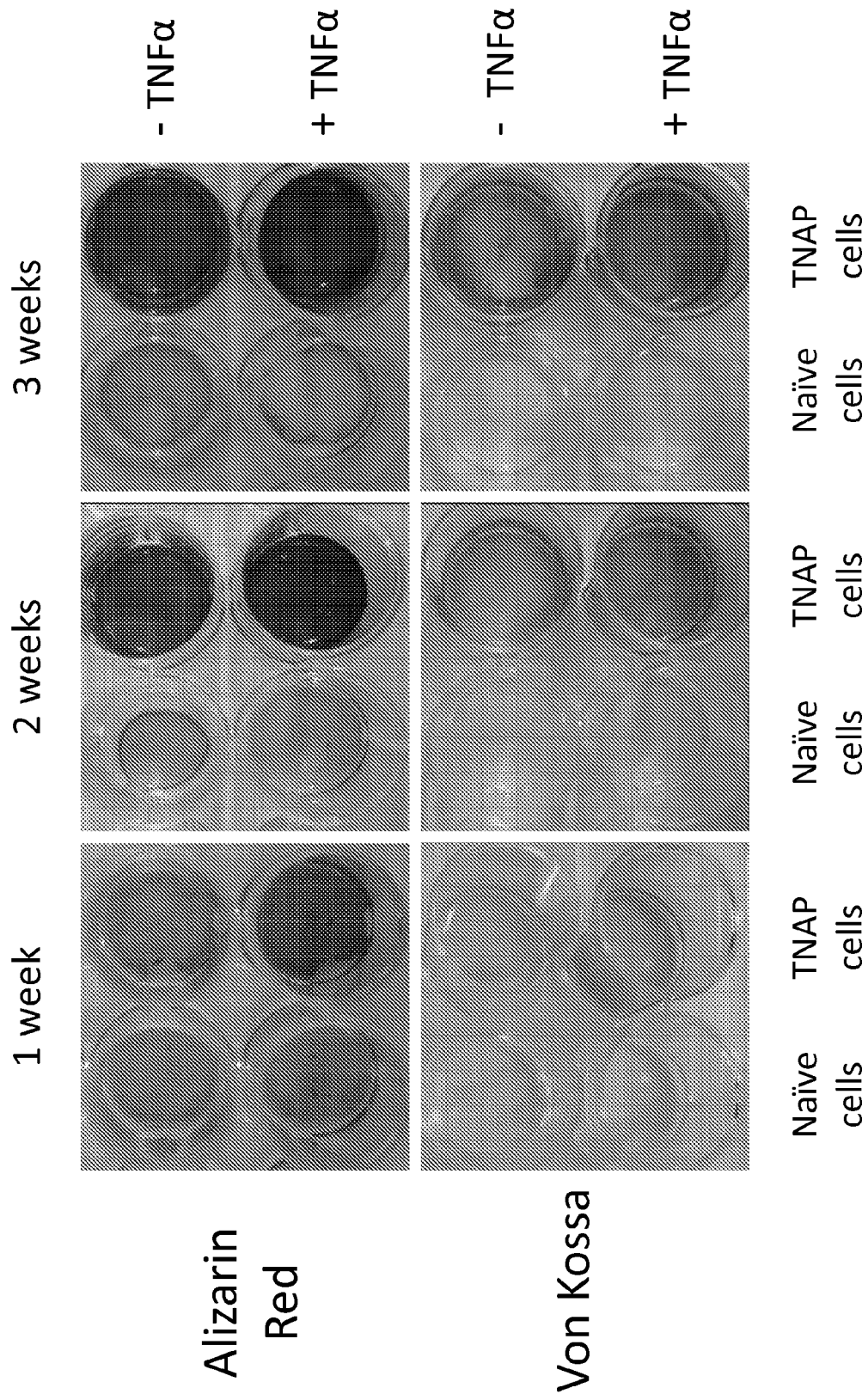
FIG. 10 shows images of Alizarin Red and Von Kossa staining of naïve BNP cells, BNP cells infected with LacZ, and BNP cells infected with TNAP, some cells additionally treated with TNF-α, at 1 week, 2 weeks, and 3 weeks.

As shown in FIG. 10, the unstimulated TNAP infected cells showed mineralization after 14 and 21 days but the staining was darker, evidencing further mineralization in the TNAP infected cells stimulated with TNF-α. NP cells stimulated with TNF-α only did not show mineralization.

Figure 11:
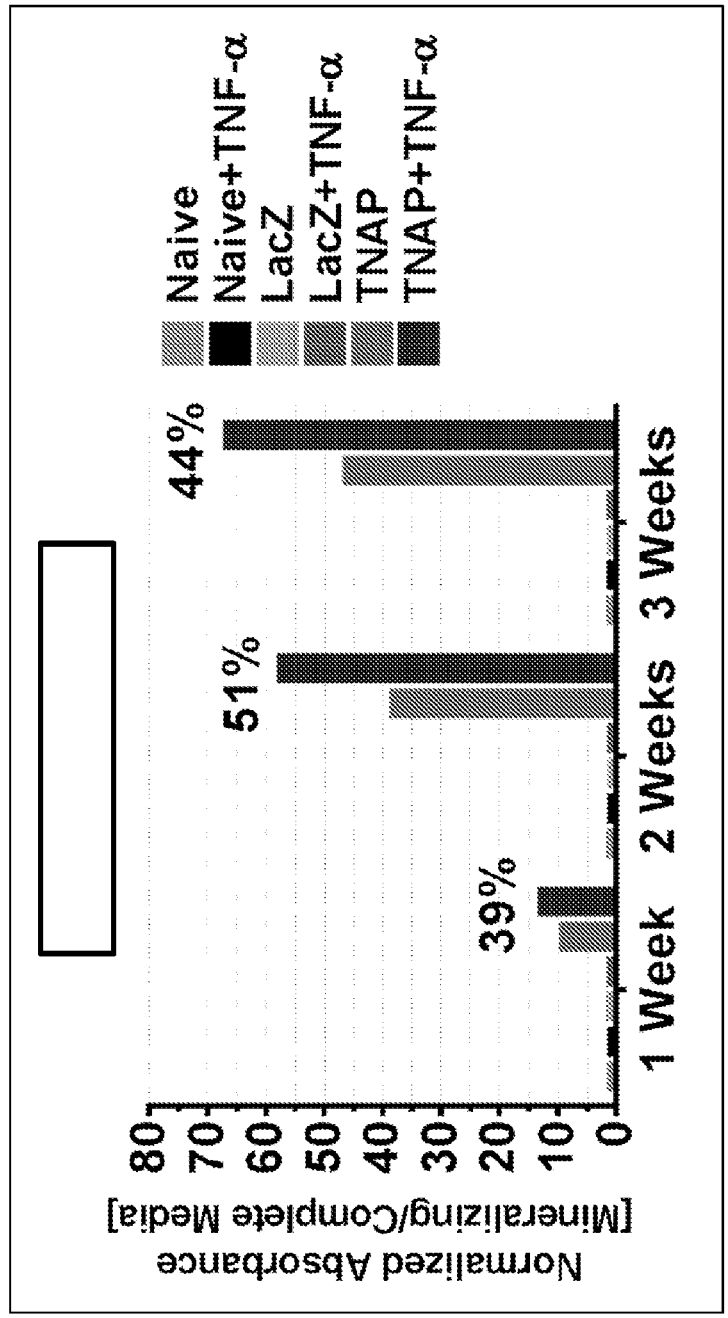
FIG. 11 is a graph depicting quantitative results of the Alizarin Red staining of the same cells shown in FIG. 10. The bars on the graph from left to right depict: naïve cells; naïve cells treated with TNF-α; cells infected with LacZ; cells infected with LacZ treated with TNF-α; cells infected with TNAP; and cells infected with TNAP and treated with TNF-α. The numbers above the bars for the TNAP+TNF-α cells indicate increase in staining activity in cells treated with TNF-α, as compared to cells infected with TNAP and not treated with TNF-α.

FIG. 11 shows quantitative results of the staining with Alizarin Red. The cells that overexpressed TNAP and are stimulated with TNF-α had an average of 45% more staining than TNAP alone over the course of three weeks.

Example 8—Over-Expression of TNF-α Using a Retroviral Vector

Materials and Methods

The NP cell culture described in Example 1 was used.

A bovine TNF-α gene was cloned (in house) into a retroviral vector, pMX-ires-neo, and viral particles generated using techniques known in the art. Bovine NP cells were transduced by spinoculation with both this retroviral vector and the one described in Example 2 to obtain a double infected cell, and selected using blasticidin and geneticin G418. LacZ in the pMX-ires-neo was used as a control vector.

TNF-α mRNA was measured using qualitative polymerase chain reaction.

Results

Figure 12:
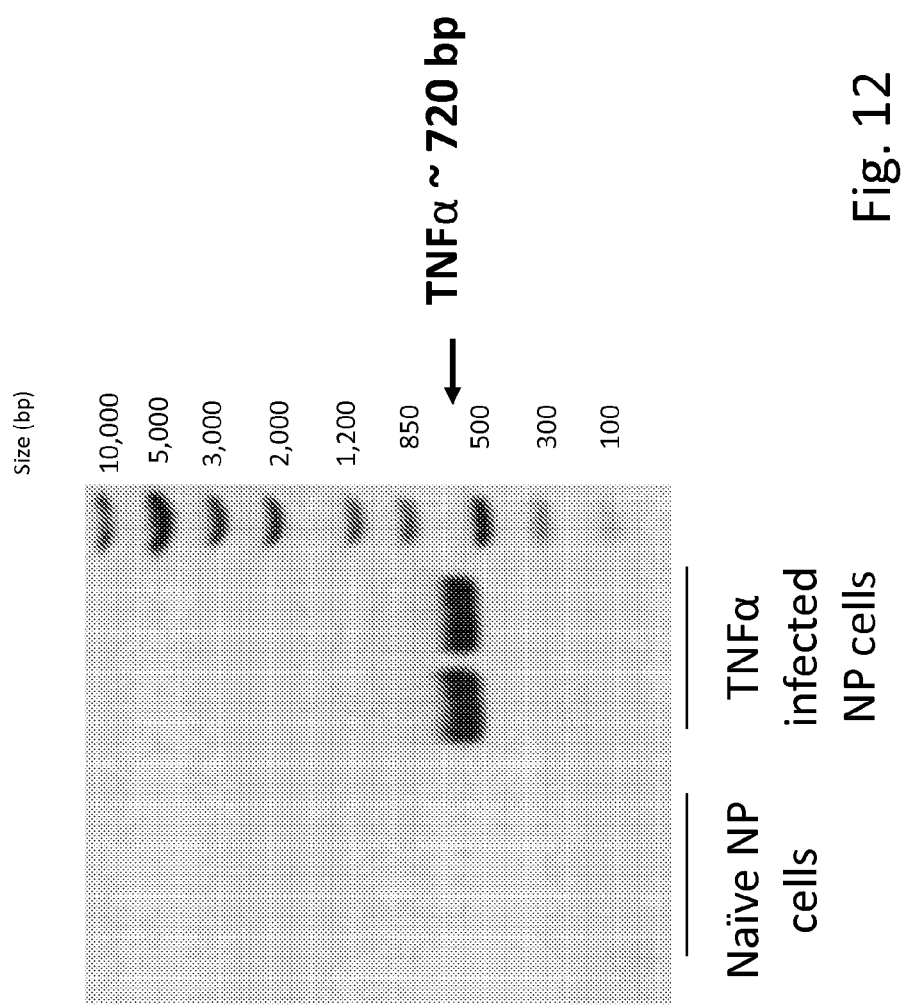
FIG. 12 is a gel showing that NP cells infected with a vector containing TNF-α expressed TNF-α.

As shown in FIG. 12, the NP cells infected with the TNFα retroviral vector overexpressed TNF-α.

Example 9—Over-Expression of TNAP and ANKH shRNA or TNF-α in Bovine NP Cells Leads to Enhanced Matrix Mineralization Materials and Methods The cells from Example 2 (TNAP infected, LacZ infected), and Example 6 (LacZ+shANKH, TNAP+shANKH), as well as cells infected with both LacZ+TNFα, and TNAP+TNFα were grown in high density cultures in a medium comprising DMEM high glucose (4.5 g/L) plus PenStrep, and 10% FBS. Some cells were grown in medium additionally containing 50 µ/ml ascorbic acid, and 5 mM of f-glycerophosphate ("mineralization medium").

The cells were stained with Alizarin Red after 1 week.

Results

Figure 13:
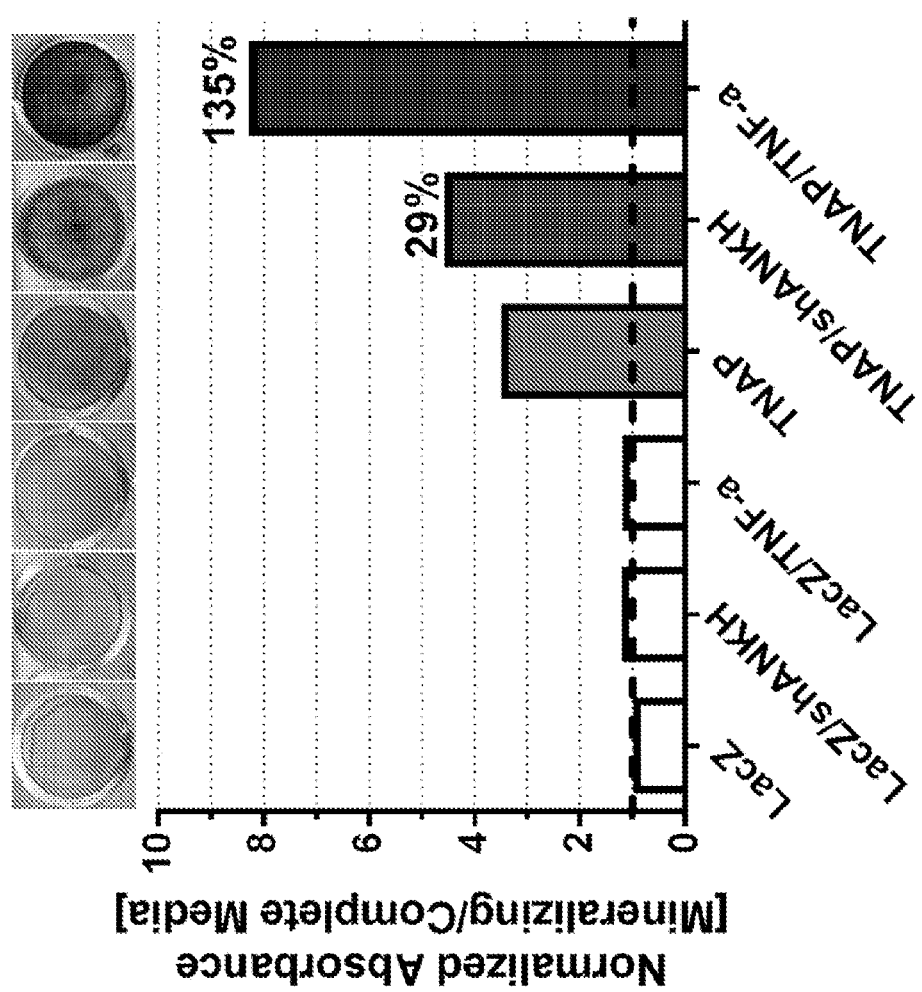
FIG. 13 shows images of Alizarin Red staining of BNP cells infected with LacZ, BNP cells infected with LacZ and shANKH, BNP cells infected with LacZ and TNF-α, BNP cells infected with TNAP alone, BNP cells infected with TNAP and shAhNKH, and BNP cells infected with TNAP and TNF-α, and a graph depicting quantitative results of the Alizarin Red staining of the same cells.

As shown qualitatively in the top panel of FIG. 13, the cells doubly infected with either TNAP and shANKH or TNF-α had darker Alizarin Red staining indicating enhanced mineralization as compared to the cells infected with only TNAP:

As shown in the graph in FIG. 13, the double infected TNAP/shANKH cells had a 29% greater staining than the cells infected with TNAP alone, and the double infected TNAP/TNFα had a 135% greater staining than the cells infected with TNAP alone again indicating enhanced mineralization.

These results indicated that the co-infection of NP cells with TNAP retrovirus and ANKH shRNA or TNF-α enhanced mineralization.

Example 10-Gene Expression Analysis

Materials and Methods

Pellet (3-D) cultures of the cells described in Examples 2, 6, 7, and 9 (cells infected with shANKH, TNF-α, or TNAP alone, cells infected with shANKH/TNAP or TNF-α/TNAP) were grown in medium containing DMEM high glucose (4.5 g/L) plus 1% Pen/Strep, 10% FBS, and 10 mM HEPES ("complete medium"). Some cells were grown in medium additionally containing 50 µ/ml ascorbic acid, and 5 mM of β-glycerophosphate ("mineralization medium"). Cultures were grown under normal or hypoxic conditions as described in Example 2.

The pellets were collected for gene expression analysis and Alizarin Red and von Kossa staining after 72 hours and 10 days.

Pellets were also immunofluorescent stained with Type X collagen antibody (Abcam, cat. # ab58632) and ProLong-Gold antifade reagent with DAPI (Molecular Probes, cat. #P36935) at 72 hours.

Gene expression was analyzed by polymerase chain reaction. Genes that were analyzed for expression were inhibitors of mineralization, ANKH and ENPP-1, chondrocyte markers, aggregan (ACAN) and collagen II (COL2A1), and hypertrophic markers, runx2 (RUNX2), collagen X (COL10A1), metallomatrix protein 13 (MMP13), and collagen I (COL1A1).

Results

Figure 14:
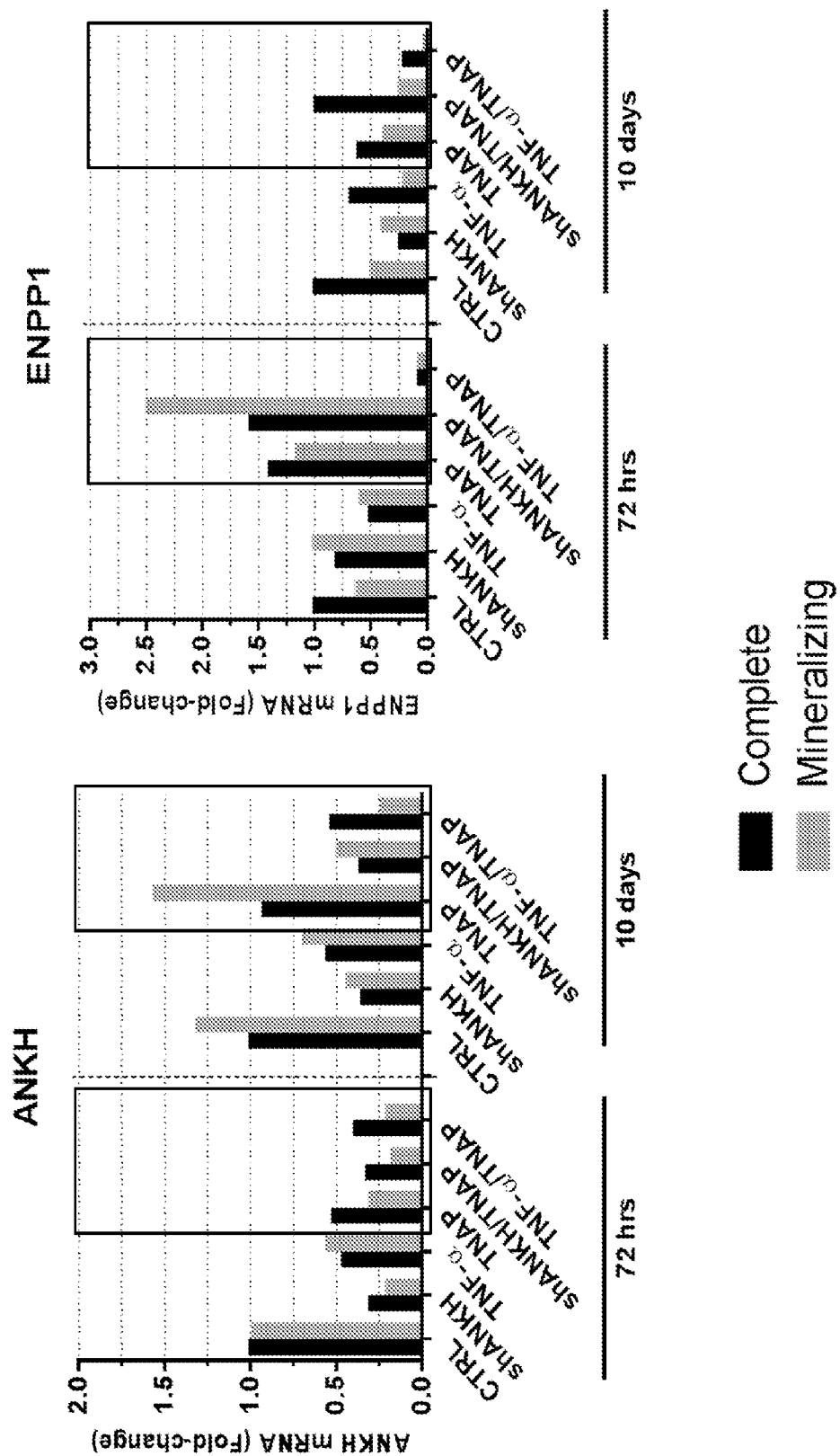
FIG. 14 are graphs of results of polymerase chain reaction for the expression of ANKH and ENPP mRNA in control BNP cells, BNP cells infected with shANKH, BNP cells infected with TNF-α, BNP cells infected with TNAP, BNP cell infected with shANKH and TNAP, and BNP cells infected with TNF-α and TNAP, at 72 hours and 10 days in complete and mineralization medium.

FIG. 14 shows the fold change in mRNA of inhibitors of mineralization, ANKH and ENPP-1. Cells that over-expressed TNAP and TNF-α also down-regulated both inhibitors of mineralization, whereas cells that infected with TNAP and shANKH down-regulated ENPP-1 only after 10 days.

Figure 15:
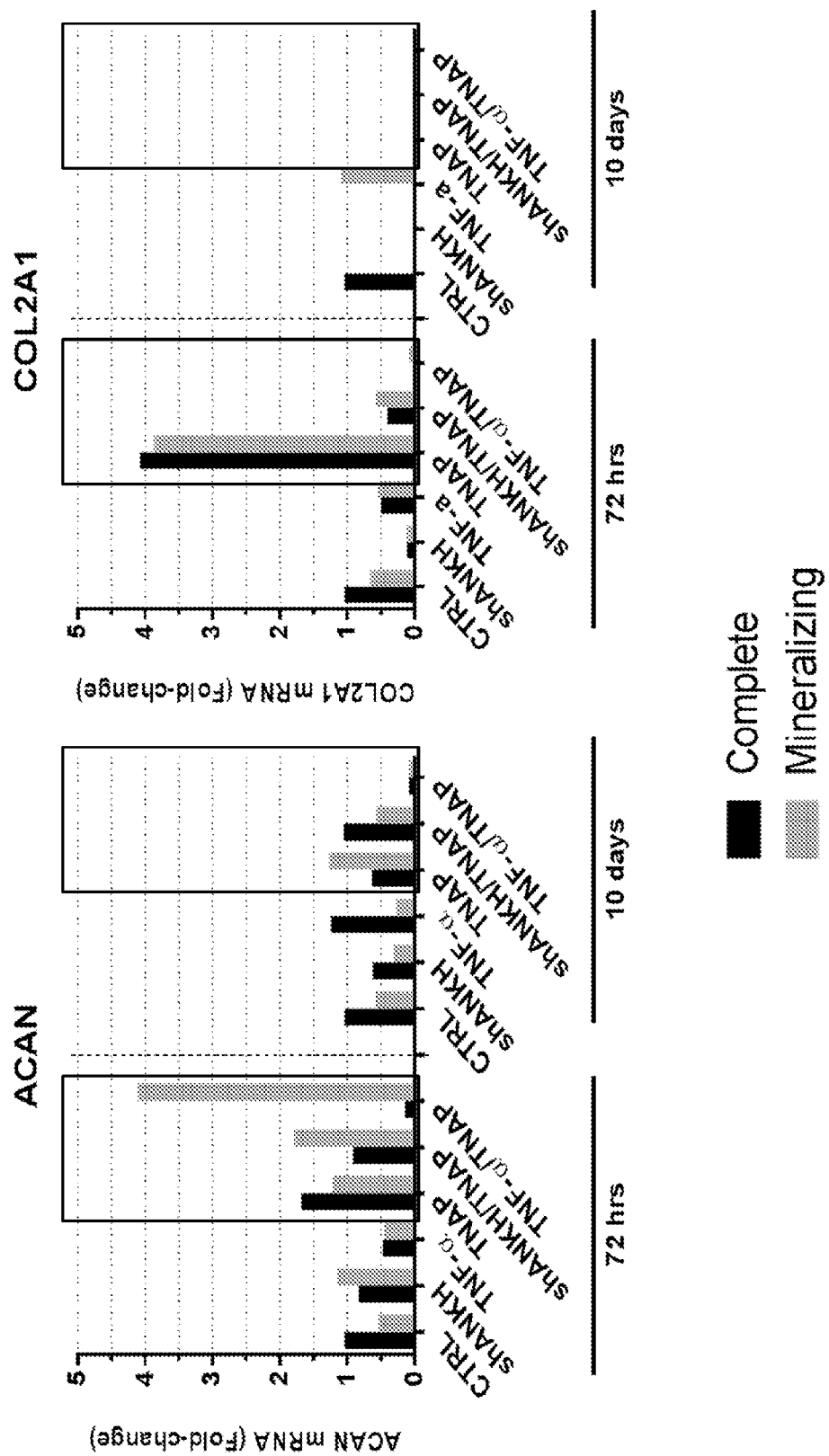
FIG. 15 are graphs of results of polymerase chain reaction for the expression of ACAN and COL2A1 mRNA in control BNP cells, BNP cells infected with shANKH, BNP cells infected with TNF-α, BNP cells infected with TNAP, BNP cell infected with shANKH and TNAP, and BNP cells infected with TNF-α and TNAP, at 72 hours and 10 days in complete and mineralization medium.

FIG. 15 shows the fold change of mRNA of chondrocyte markers ACAN and COL2A1. Cells that over-expressed TNAP and TNF-α down-regulated both ACAN and COL2A1 at the later time point of 10 days. Additionally cells infected with only TNAP, and TNAP and shANKH also down regulated COL2A1 at 10 days.

Figure 16:
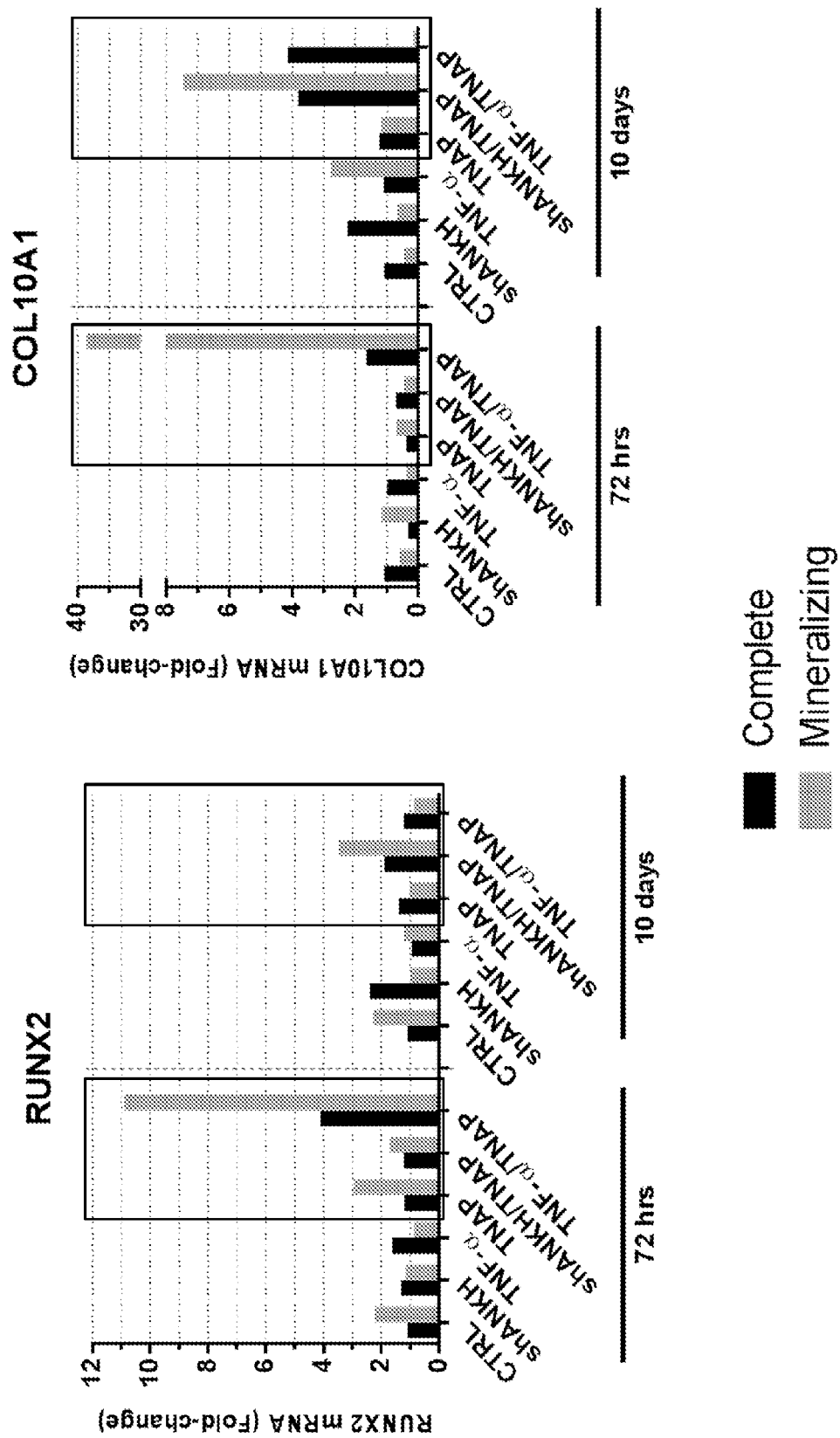
FIG. 16 are graphs of results of polymerase chain reaction for the expression of RUNX2 and COL10A1 mRNA in control BNP cells, BNP cells infected with shANKH, BNP cells infected with TNF-α, BNP cells infected with TNAP, BNP cell infected with shANKH and TNAP, and BNP cells infected with TNF-α and TNAP, at 72 hours and 10 days in complete and mineralizing medium.
Figure 17:
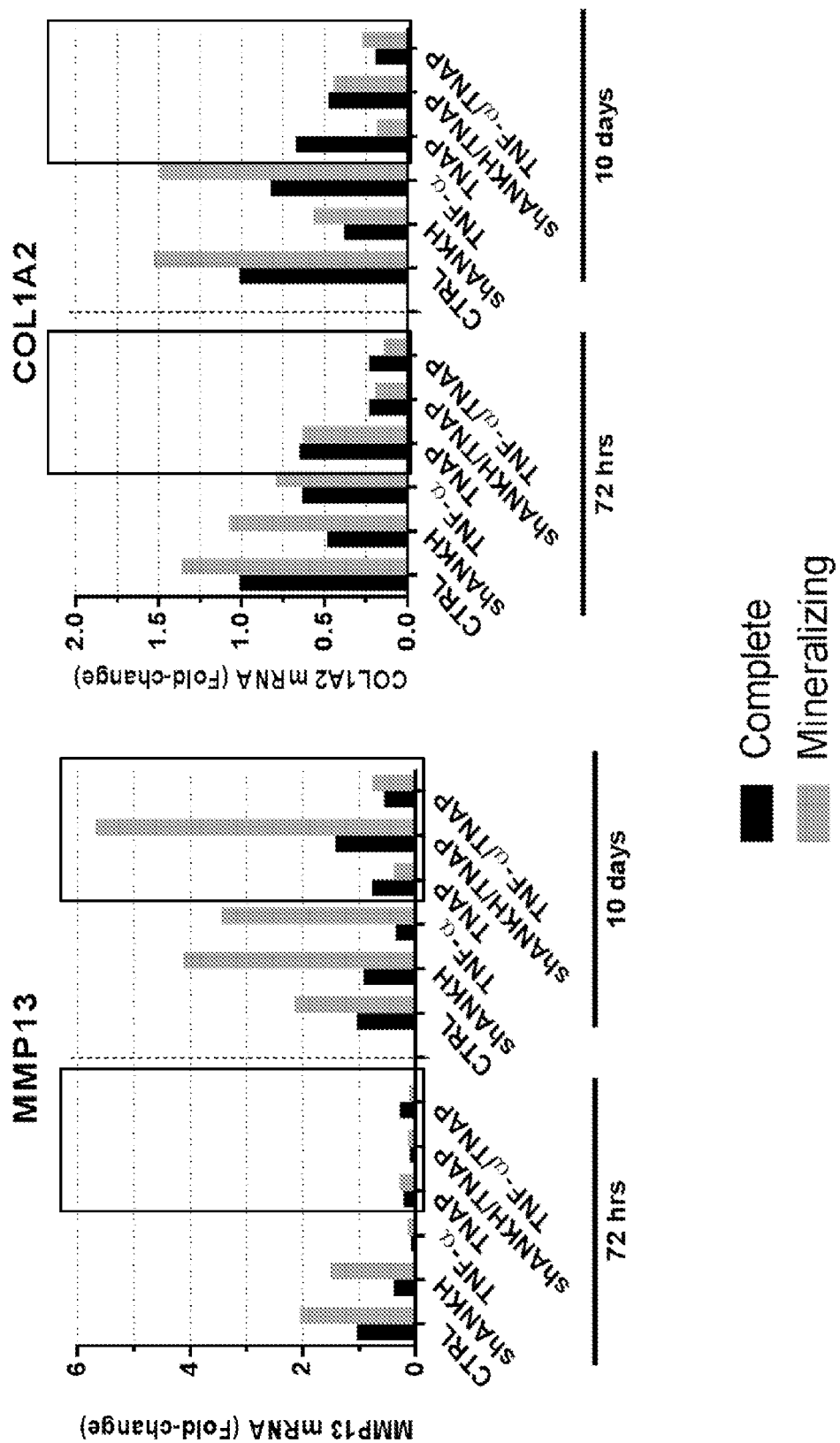
FIG. 17 are graphs of results of polymerase chain reaction for the expression of MMP13 and COL1A2 mRNA in control BNP cells, BNP cells infected with shANKH, BNP cells infected with TNF-α, BNP cells infected with TNAP, BNP cell infected with shANKH and TNAP, and BNP cells infected with TNF-α and TNAP, at 72 hours and 10 days in complete and mineralization medium.

FIGS. 16 and 17 show the fold change of mRNA of hypertrophic markers. RUNX2 and COL10A were up-regulated after 72 hours in cells over-expressing TNAP and TNF-α in mineralization medium. RUNX2, COL10A1, and MMP13 were also up-regulated in TNAP/shANK cells after 10 days in mineralization medium.

The mineralization kinetics was the same in the pellet cultures as in the 2-D cultures with mineralization being accelerated in the TNAP/TNF-α cells (data not shown).

Figure 18B:
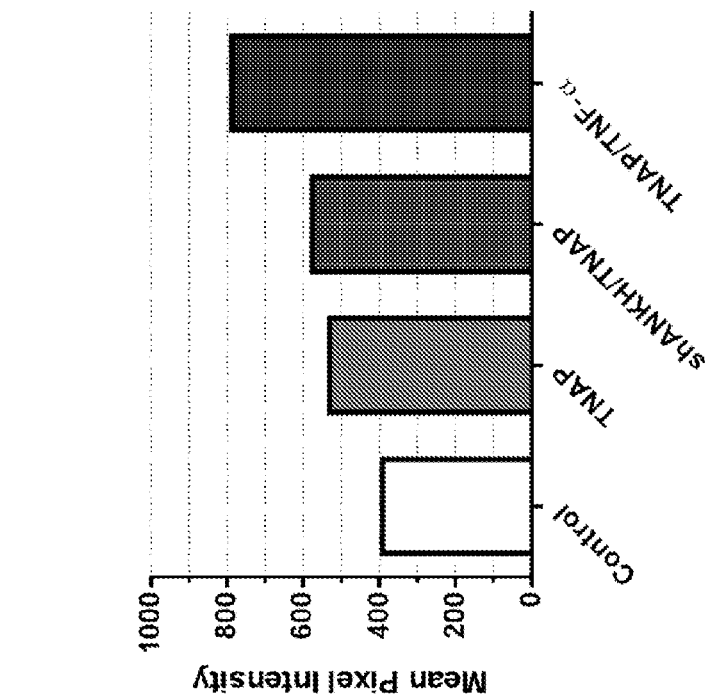
FIG. 18B is a graph quantifying the results shown in FIG. 18A.
Figure 18A:
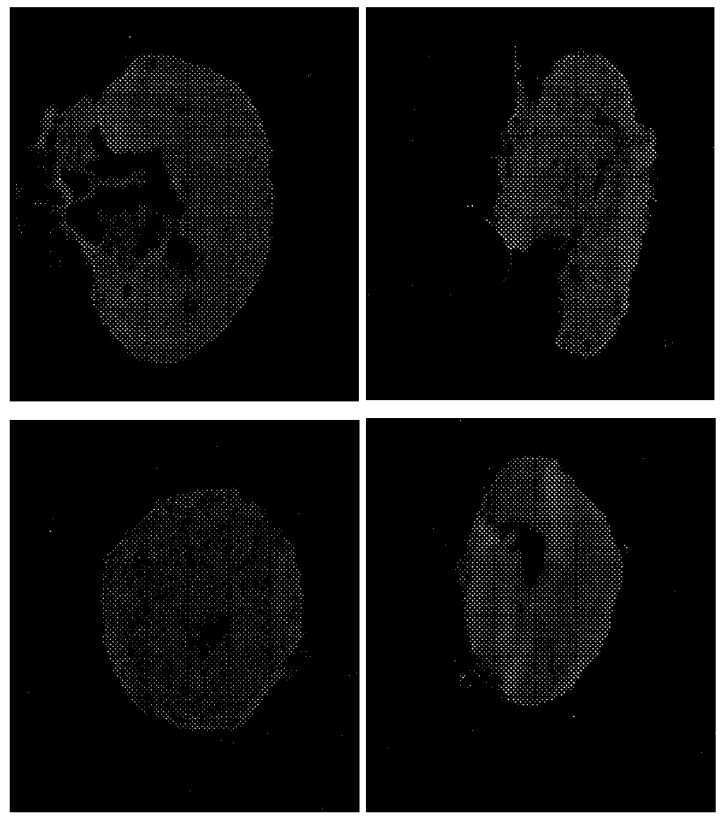
FIG. 18A are images of the immunostaining of native BNP cells, BNP cells infected with TNAP, BNP cell infected with shANKH and TNAP, and BNP cells infected with TNF-α and TNAP with collagen X.

Additionally, the cells that over-expressed TNAP and TNF-α had more intense staining for collagen X after 72 hours in mineralization medium than cells overexpressing TNAP alone, and those infected with TNAP and shANKH (FIGS. 18A and B), indicating these cells expressed more collagen, and correlated to the COL10A1 mRNA increase observed at the same time point for the TNAP/TNF-α pellets.

Example 11—Over-Expression of TNAP and TNF-α in Bovine NP Cells Induced Mineralization in Rabbit Discs Materials and Methods Rabbit disc cultures as described in Example 3, were injected with the cells from Examples 2, 5, and 7 (TNAP infected, TNAP and ANKH shRNA co-infected, TNAP and TNF-α co-infected, and naïve) and the discs were incubated for four weeks in mineralization medium and collected and fixed with 10% NB formalin overnight and kept in 70% ethanol. The discs were analyzed for mineralization by high definition x-ray and microCT to quantify mineralization.

Results

Figure 19:
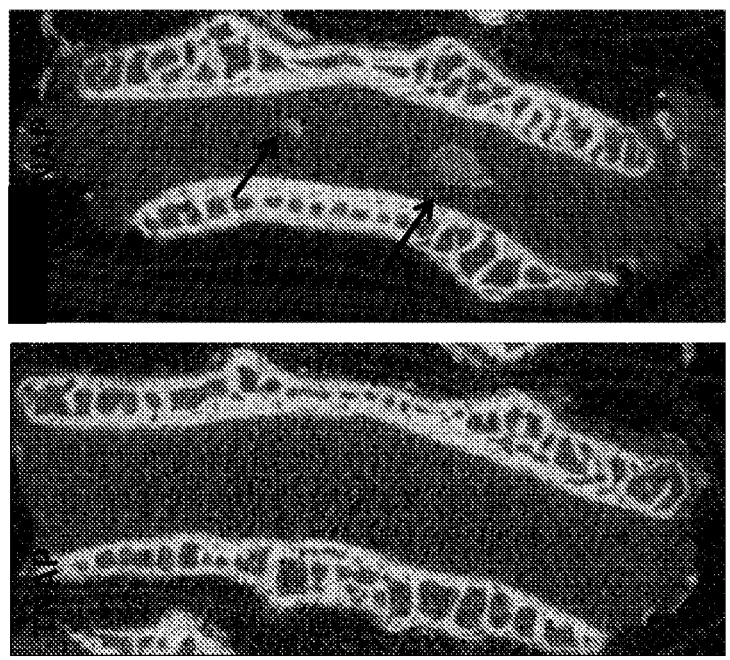
FIG. 19 are microCT images of discs injected with BNP cells overexpressing TNAP and TNF-α (right hand panel) and injected with cells overexpressing TNAP only (left hand panel). The arrows in the right hand panel denote mineralization.

X-rays show mineralization of the disc was observed in discs injected with TNAP and TNF-α over-expressing NP cells. As shown in FIG. 19, the arrows denote mineralization only in the disc injected TNAP and TNF-α over-expressing NP cells (right hand panel).

MicroCT showed the same result, with the discs treated with cells co-infected with TNAP and TNF-α having increased bone volume (BV). Total volume was similar for both discs (TV). See Table 2 and FIG. 20.

Figure 20:
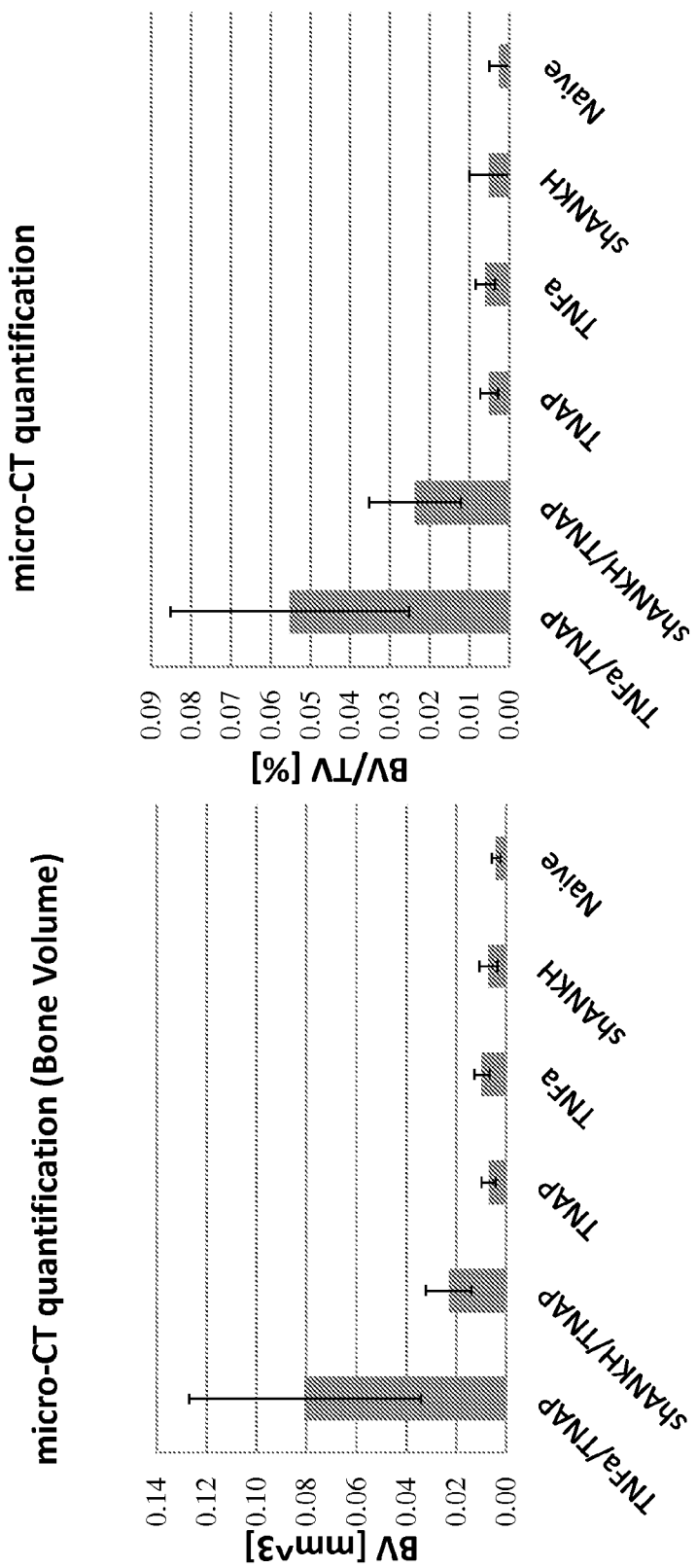
FIG. 20 are graphs of microCT results (bone volume and ratio of bone volume to total volume) of discs injected with naïve BNP cells, BNP cells infected with TNAP, BNP cells infected with TNF-α, BNP cells infected with ahANKH, BNP cell infected with shANKH and TNAP, and BNP cells infected with TNF-α and TRAP FIG. 21 are images and a graph depicting the results of Alizarin Red staining of NP cells infected with LacZ or TNAP and treated with 0.01 ng/ml of IL-1β or 2 ng/ml of IL-1β after 7 days.

MicroCT also showed that cells co-infected with TNAP and ANKH shRNA also generated mineralization in the discs (FIG. 20).

TABLE 2

Bone Volume as Measured by microCT in Rabbit Discs injected with Bovine NP Cells Co-infected with TNAP and TNF, and Infected with TNAP alone

|  | TV | BV | BV/TV |
|---|---|---|---|
| TNAP | 159.8 | 0.019 | 0.0001 |
| TNAP/TNF | 157.9 | 1.045 | 0.0066 |

TV—total volume (disc)
BV—Bone volume (mineral formed)

Example 12—Effect of IL-1β B on Mineralization

Materials and Methods

Cells from Example 2 were grown in mineralization medium in the presence or absence of a low dose of IL-1A (0.01 ng/ml) or a high dose (2 ng/ml) (R&D Systems). Cells were analyzed by Alizarin Red staining at 7 and 10 days as previously described. RT-PCR analysis of ANK and ENPP was also performed as previously described, using primers specific for ANKH and ENPP1.

Results

Figures 21, 22:
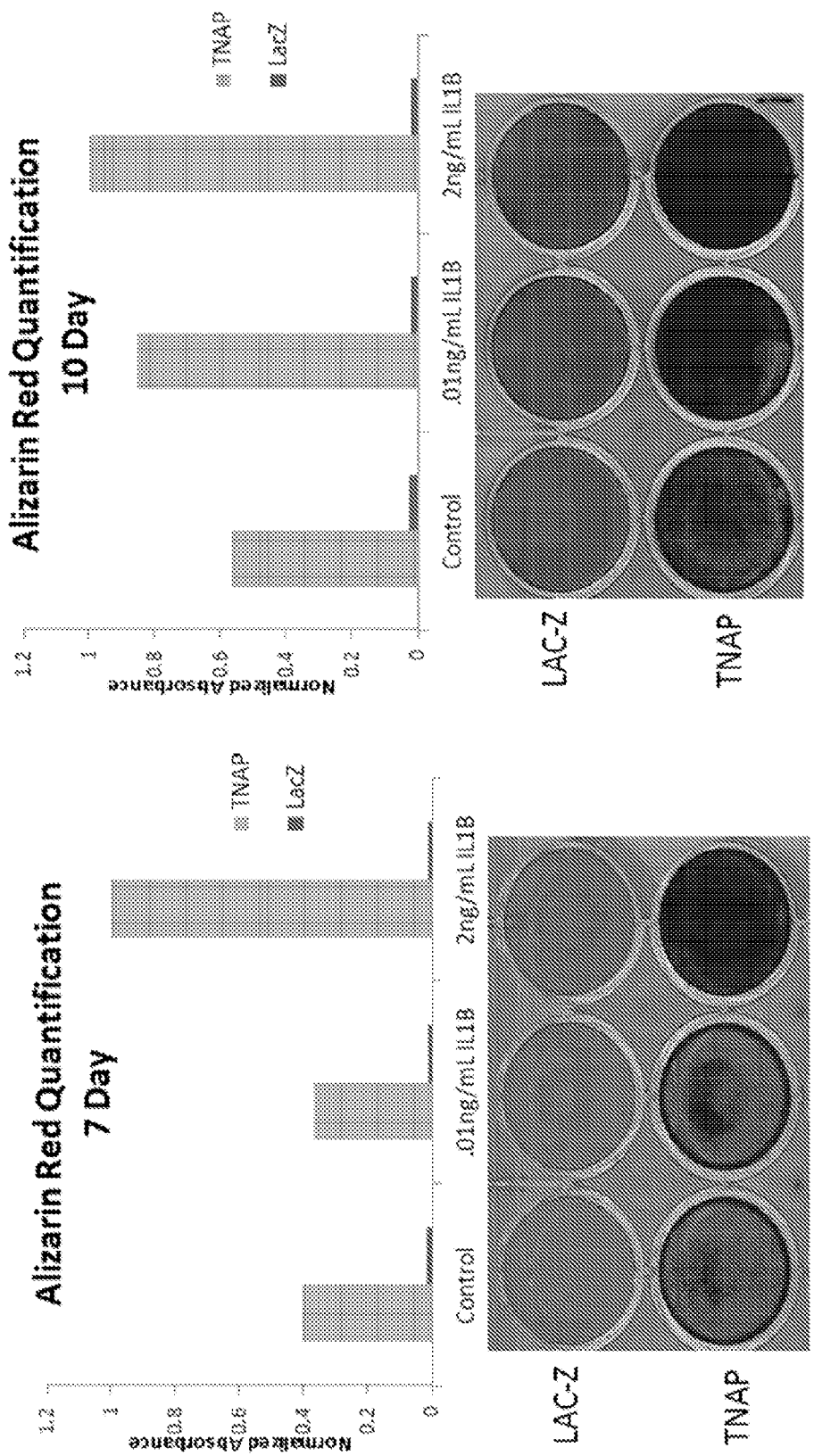
FIG. 22 are images and a graph depicting the results of Alizarin Red staining of NP cells infected with LacZ or TNAP and treated with 0.01 ng/ml of IL-1β or 2 ng/ml of IL-1β after 10 days.

A dose-dependent increase in calcium staining of TNAP-infected BNP cell cultures was observed with Alizarin Red, indicating increased matrix deposition at 7 (FIG. 21) and 10 days (FIG. 22) when treated with IL-1β. There was no observable change in staining for NP cells transduced with LacZ.

Figure 23:
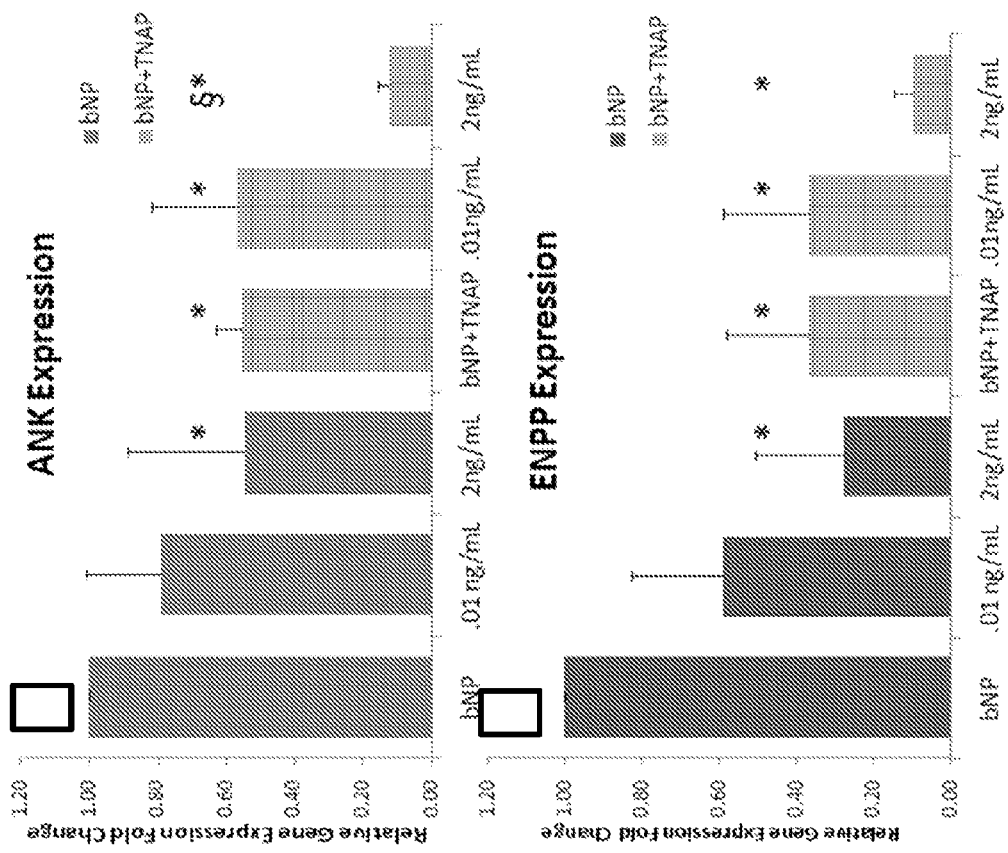
FIG. 23 are graphs depicting the results of polymerase chain reaction for the expression of ANKH and ENPP mRNA in control BNP cells, BNP cells, treated with 0.01 ng/ml of IL-1β or 2 ng/ml of IL-1β, BNP cells infected with TNAP, untreated and treated with 0.01 ng/ml of IL-1β or 2 ng/ml of IL-1β at day 3.

A dose-dependent decrease in the transcripts ANK and ENPP was also observed with IL-1β treatment in cultured naïve cells and TNAP-infected BNP cells (FIG. 23).

Example 13—Cells Co-Infected with TNAP and TNF-α Behave Like Bone

Materials and Methods

Figure 24A:
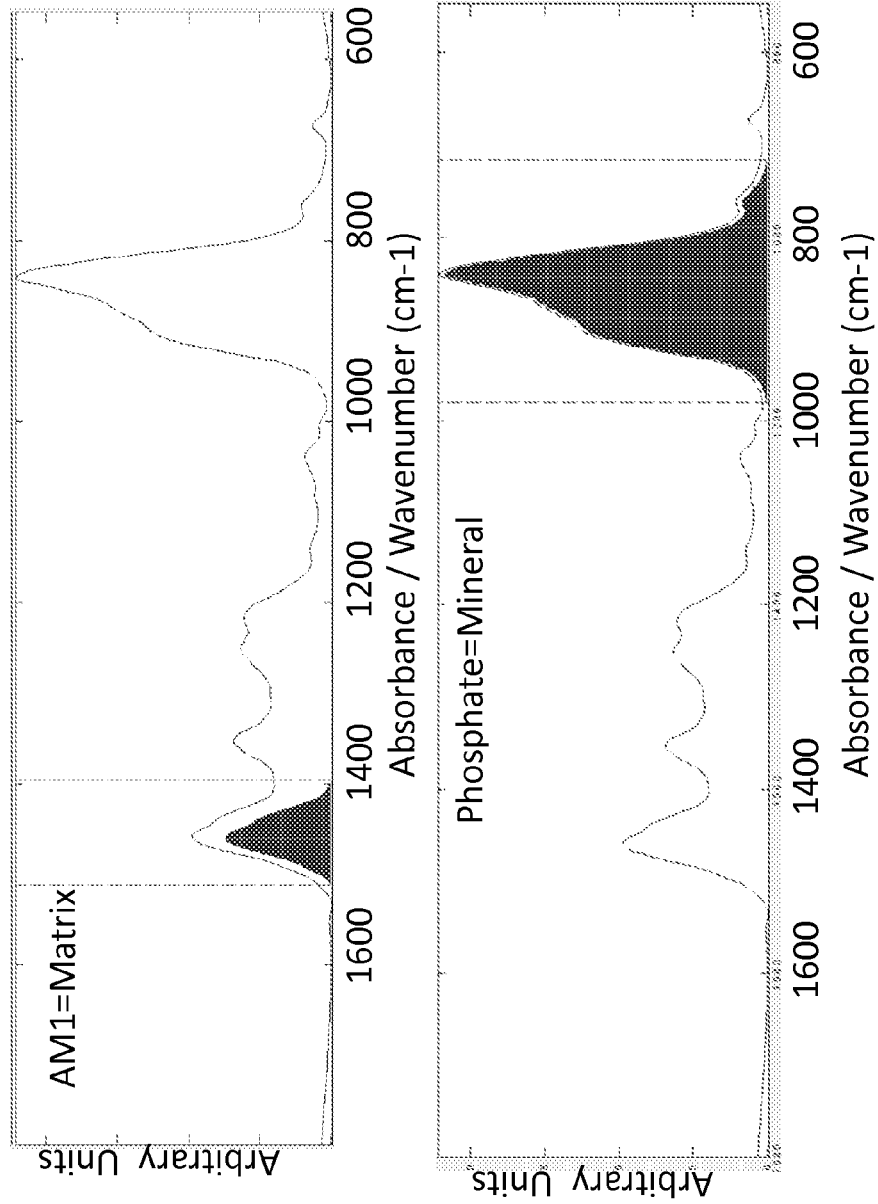
FIG. 24A are FTIR parameters used for the matrix and mineral analysis.

Fourier Transform Infrared spectroscopy (FTIR) analysis of mineral produced by cells from Examples 2, 5, and 7 (TNAP infected, TNAP and ANKH shRNA co-infected, TNAP and TNF-α co-infected) was performed. Mouse bone and hydroxyapatite were used as controls. FIG. 24A shows the FTIR parameters used for matrix and mineral.

Results

Figure 24B:
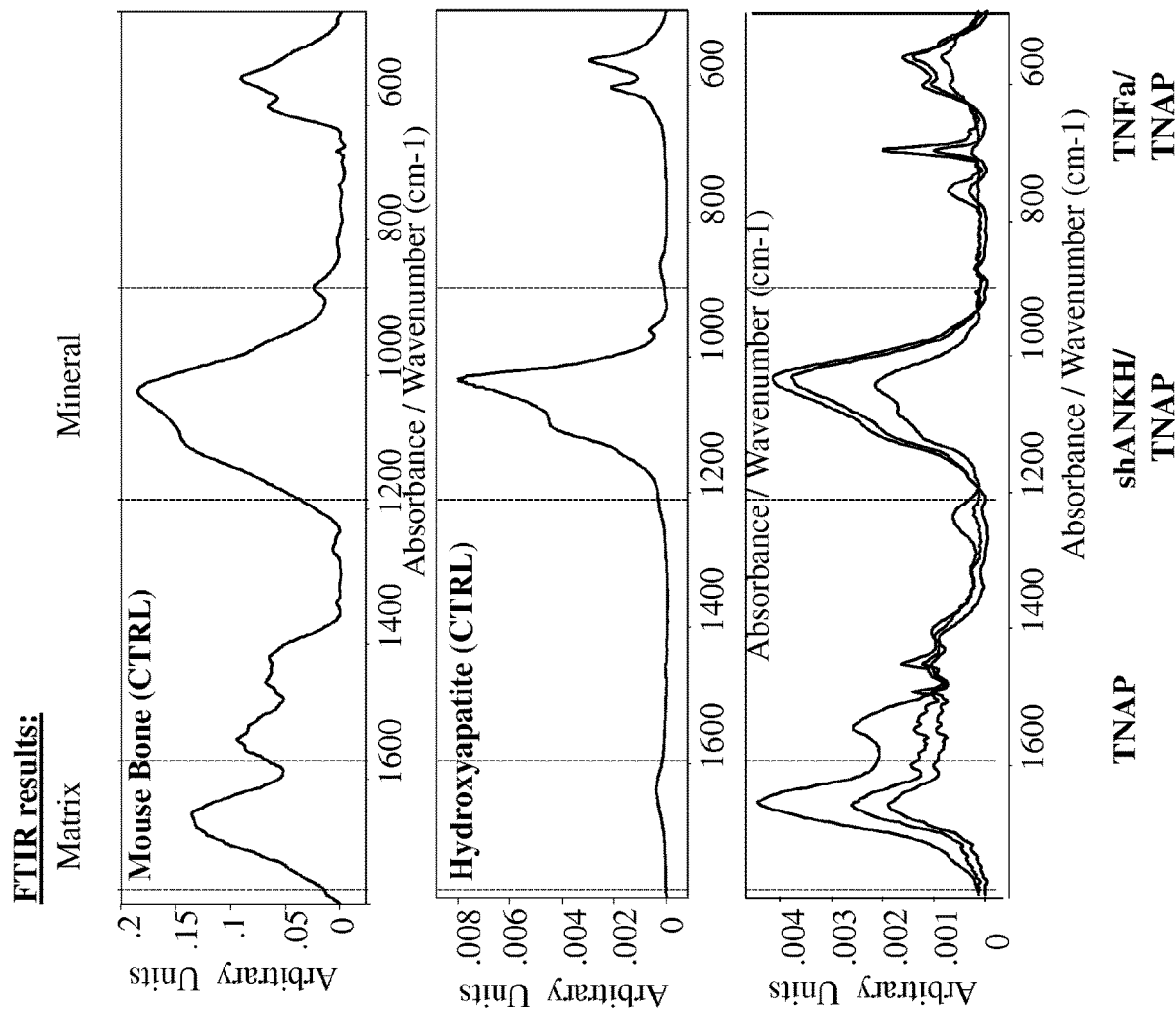
FIG. 24B are the results of the FTIR analysis on controls, mouse hone and hydroxyapatite, and BNP cells infected with TNAP, BNP cell infected with shANKH and TNAP, and BNP cells infected with TNF-α and TNAP.

The top panels of FIG. 24B show the results for mouse bone and hydroxyapatite with a peak for the formation of bone mineral at an absorbance of about 1020. The lower panel in FIG. 24B is the analysis of the cell samples, and indicated that the TNAP/TNF-α co-infected cells behaved the most like bone.

These results correlated to other parameters from the FTIR found in Table 3.

TABLE 3

Additional Parameters from FTIR Analysis

| Sample | Mineral/ Matrix | Crosslink (Ratio 1660/1690) | Crystallinity (Ratio 1030/1020) | HA Acidity (Ratio 1127/1096) |
|---|---|---|---|---|
| Mouse Bone | 7.88 | 2.70 | 1.23 | 0.47 |
| Hydroxyapatite |  |  | 1.35 | 0.50 |
| TNAP/TNF-α | 7.38 | 1.00 | 1.00 | 0.50 |
| TNAP/shANKH | 4.74 | 2.00 | 1.33 | 0.50 |
| TNAP | 1.42 | 3.00 | 1.00 | 1.00 |

REFERENCES

Ambros (2004) *Nature* 431:350
Anderson (2003) *Current Rheumatol. Reports* 5:222
Baroy et al. (2010) *Mol. Biotechnol.* 45: 116.
Bartel (2009) *Cell* 136:215
Buchet et al. (2013) *Methods in Molecular Biology* 1053: 115
Cheng and Pritzker (1983) *J Rheum.* 10:796
Coe et al. (2006) *Spine* 31:345
Cunningham et al. (2010) *Clin. Orthop. Relat. Res.* 468: 2695
DiMauro et al. (2002) *J. Bone Miner. Res.* 17:1383
Gurley et al. (2006) *J. Bone. Miner. Res.* 21:1238
Gregory et al. (2004) *Analytical Biochemistry* 329:77
Krebs et al. (2009) *J. Biomed. Material Res.* 92:1131
Koshizuka et al. (2001) *Cytogenet. Cell Genet.* 94:163
Minogue et al. (2010) *Arthritis and Rheumatism* 62:3695
Murshed et al. (2005) *Genes and Development* 19:1093
Ong et al. (2007) *Orthopedic Research Society*, 53rd Annual Meeting
Rajaee et al. (2012) *Spine* 37:67
Rutsch et al. (2003) *Nature Genetics* 34:379
Skubutyte et al. (2010) *Arthritis and Rheumatism* 62:2707
Zhao et al. (2012) *Kidney International* 82:34

The invention claimed is:

1. An isolated genetically modified nucleus pulposus cell which causes the mineralization of intervertebral disc tissue, comprising a nucleic acid encoding tissue-nonspecific alkaline phosphatase associated with a heterologous promoter, and an agent or agents which decreases the expression of the gene encoding progressive ankylosis or the amount or activity of progressive ankylosis chondrocytes.

2. The isolated genetically modified nucleus pulposus cell of claim 1, wherein the cell has markers of a hypertrophic chondrocyte.

3. An isolated genetically modified nucleus pulposus cell which causes the mineralization of intervertebral disc tissue, comprising a nucleic acid encoding tissue-nonspecific alkaline phosphatase associated with a heterologous promoter, and an agent or agents which decreases the expression of the gene encoding plasma cell membrane glycoprotein (PC-1)/ectonucleotide pyrophosphatase/phosphodiesterase-1 or the amount or activity of plasma cell membrane glycoprotein (PC-1)/ectonucleotide pyrophosphatase/phosphodiesterase-1.

4. The isolated genetically modified nucleus pulposus cell of claim 1, wherein the cell has markers of a hypertrophic chondrocyte.

* * * * *

SEQUENCE LISTING

```
<160> NUMBER OF SEQ ID NOS: 3

<210> SEQ ID NO 1
<211> LENGTH: 61
<212> TYPE: DNA
<213> ORGANISM: Bos taurus
<220> FEATURE:
<221> NAME/KEY: misc_feature
<222> LOCATION: (7)..(25)
<223> OTHER INFORMATION: n is a, c, g, or t
<220> FEATURE:
<221> NAME/KEY: misc_feature
<222> LOCATION: (35)..(53)
<223> OTHER INFORMATION: n is a, c, g, or t

<400> SEQUENCE: 1
gatccgnnnn nnnnnnnnn nnnnnttcaa gagannnnnn nnnnnnnnnn nnncttttttt    60 g                                                                   61

<210> SEQ ID NO 2
<211> LENGTH: 61
<212> TYPE: DNA
<213> ORGANISM: Bos taurus
<220> FEATURE:
<221> NAME/KEY: misc_feature
<222> LOCATION: (3)..(21)
<223> OTHER INFORMATION: n is a, c, g, or t
<220> FEATURE:
<221> NAME/KEY: misc_feature
<222> LOCATION: (31)..(49)
<223> OTHER INFORMATION: n is a, c, g, or t

<400> SEQUENCE: 2
gcnnnnnnnn nnnnnnnnnn naagttctct nnnnnnnnnn nnnnnnnnng aaaaaactta    60
a                                                                   61

<210> SEQ ID NO 3
<211> LENGTH: 51
<212> TYPE: RNA
```

```
<213> ORGANISM: Bos taurus
<220> FEATURE:
<221> NAME/KEY: misc_feature
<222> LOCATION: (2)..(20)
<223> OTHER INFORMATION: n is a, c, g, or u
<220> FEATURE:
<221> NAME/KEY: misc_feature
<222> LOCATION: (30)..(48)
<223> OTHER INFORMATION: n is a, c, g, or u

<400> SEQUENCE: 3
gnnnnnnnnn nnnnnnnnnn uucaagagan nnnnnnnnnn nnnnnnnncu u          51
```